(12) United States Patent
Old et al.

(10) Patent No.: US 8,357,373 B2
(45) Date of Patent: Jan. 22, 2013

(54) METHODS FOR STIMULATING AN IMMUNE RESPONSE USING BACTERIAL ANTIGEN DELIVERY SYSTEM

(75) Inventors: Lloyd J. Old, New York, NY (US); Gerd Ritter, New York, NY (US); Hiroyoshi Nishikawa, New York, NY (US); Sacha Gnjatic, New York, NY (US); Jorge E. Galan, New Haven, CT (US)

(73) Assignees: Ludwig Institute for Cancer Research, New York, NY (US); Yale University, New Haven, CT (US)

( * ) Notice: Subject to any disclaimer, the term of this patent is extended or adjusted under 35 U.S.C. 154(b) by 708 days.

(21) Appl. No.: 12/083,188

(22) PCT Filed: Oct. 3, 2006

(86) PCT No.: PCT/US2006/038804
§ 371 (c)(1),
(2), (4) Date: Aug. 5, 2009

(87) PCT Pub. No.: WO2007/044406
PCT Pub. Date: Apr. 19, 2007

(65) Prior Publication Data
US 2009/0324651 A1    Dec. 31, 2009

Related U.S. Application Data

(60) Provisional application No. 60/723,573, filed on Oct. 4, 2005.

(51) Int. Cl.
*A61K 39/00* (2006.01)
*A01N 63/00* (2006.01)

(52) U.S. Cl. .................. 424/184.1; 424/93.1; 424/93.2; 424/93.4

(58) Field of Classification Search ........................ None
See application file for complete search history.

(56) References Cited

FOREIGN PATENT DOCUMENTS

| WO | WO 98/53854 A1 | 12/1998 |
| WO | WO 99/55364 A2 | 11/1999 |
| WO | WO 00/59537 A1 | 12/2000 |

OTHER PUBLICATIONS

Evans, D.T. et al., "Mucosal Priming of Simian Immunodeficiency Virus-Specific Cytotoxic T-Lymphocyte Response in Rhesus Macaques by the *Salmonella* Type III Secretion Antigen Delivery System," *Journal of Virology* l 77(4):2400-2409 (2003).
Galán, J.E. et al., "In vivo antigen delivery by a *Salmonella* type III secretion system for therapeutic cancer vaccine development," *Cancer Immunity* 6 Suppl. 1:9 (2006).
Germeau, C. et al., "High frequency of antitumor T cells in the blood of melanoma patients before and after vaccination with tumor antigens," *The Journal of Experimental Medicine* 201(2):241-248 (2005).
Lurquin, C. et al., "Contrasting frequencies of antitumor and antivaccine T cells in metastases of a melanoma patient vaccinated with a MAGE rumor antigen," *The Journal of Experimantal Medicine* 201(2):249-257 (2005).
Nishikawa, H. et al., "In vivo antigen delivery by a *Salmonella typhimurium* type III secretion system for therapeutic cancer vaccines," *The Journal of Clinical Investigation* 116(7):1947-1954 (2006).
Rüssmann, H. et al., "Delivery of Epitopes by the *Salmonella* Type III Secretion System for Vaccine Development," *Science* 281:565-568 (1998).
Schoen, C. et al., "Bacteria as DNA vaccine carriers for genetic immunization," *International Journal of Medical Microbiology* 294:319-335 (2004).
Sevel Doménech, V.E. et al., "Rapid clearance of a recombinant *Salmonella* vaccine carrier prevents enhanced antigen-specific CD8 T-cell responses after oral boost immunizations," *Microbes and Infection* 7:860-866 (2005).
Wyant, T.L. et al., "*Salmonella typhi* Flagella Are Potent Inducers of Proinflammatory Cytokine Secretion by Human Monocytes," *Infection and Immunity* 67(7):3619-3624 (1999).
Yee, C., "Adoptive T cell therapy: Addressing challenges in cancer immunotherapy," *Journal of Translation Medicine* 3:17 1-8 (2005).

*Primary Examiner* — Albert Navarro
(74) *Attorney, Agent, or Firm* — Wolf, Greenfield & Sacks, P.C.

(57) ABSTRACT

The invention relates to the use of the type III secretion system of bacteria to stimulate immune responses against tumor antigen(s) for treating antigen-loss variant tumors. Methods are provided for stimulating and/or increasing an immune response against tumor antigens. The invention also relates to the preparation of antigen presenting cells from peripheral blood mononuclear cells using bacteria having a type III secretion system.

28 Claims, 12 Drawing Sheets

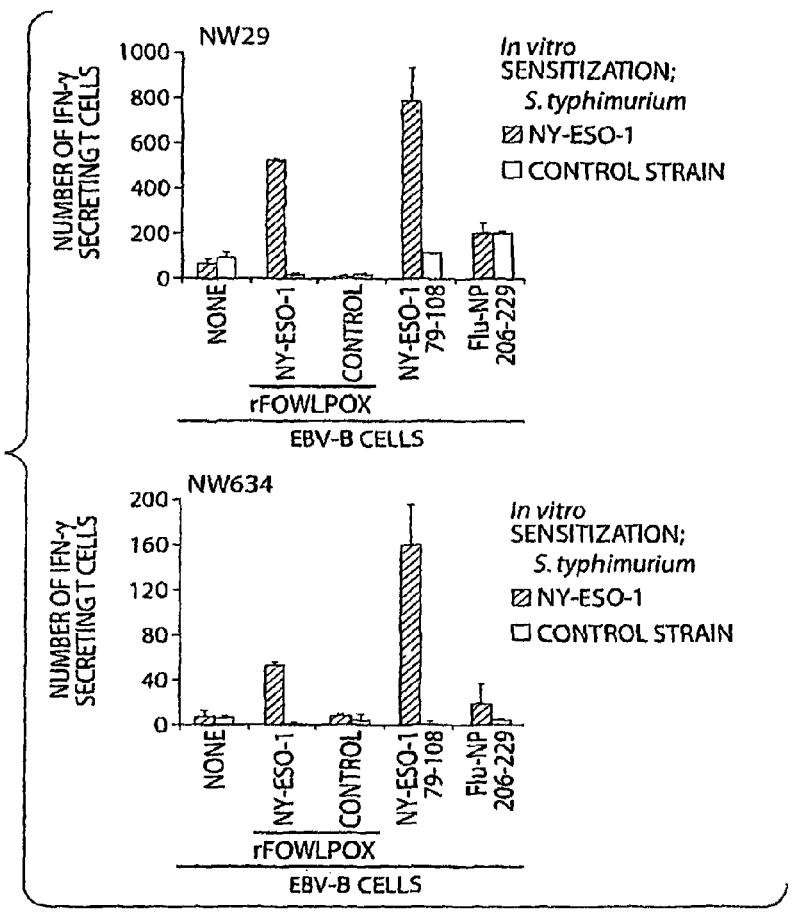
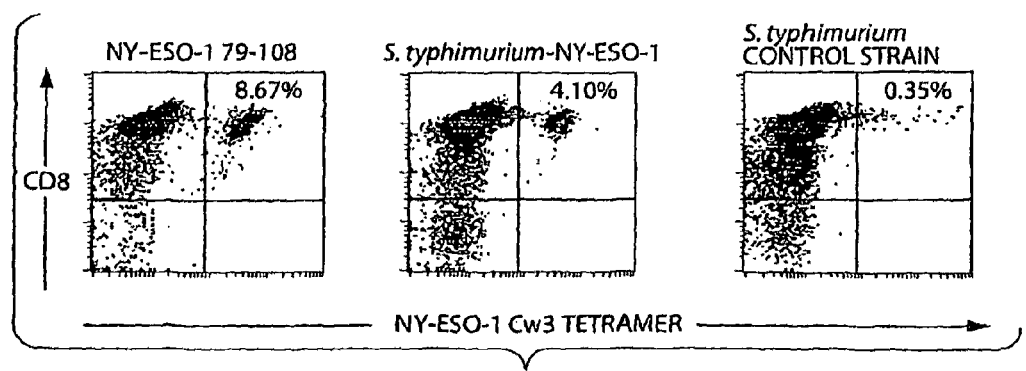
Fig. 3A
Fig. 3B

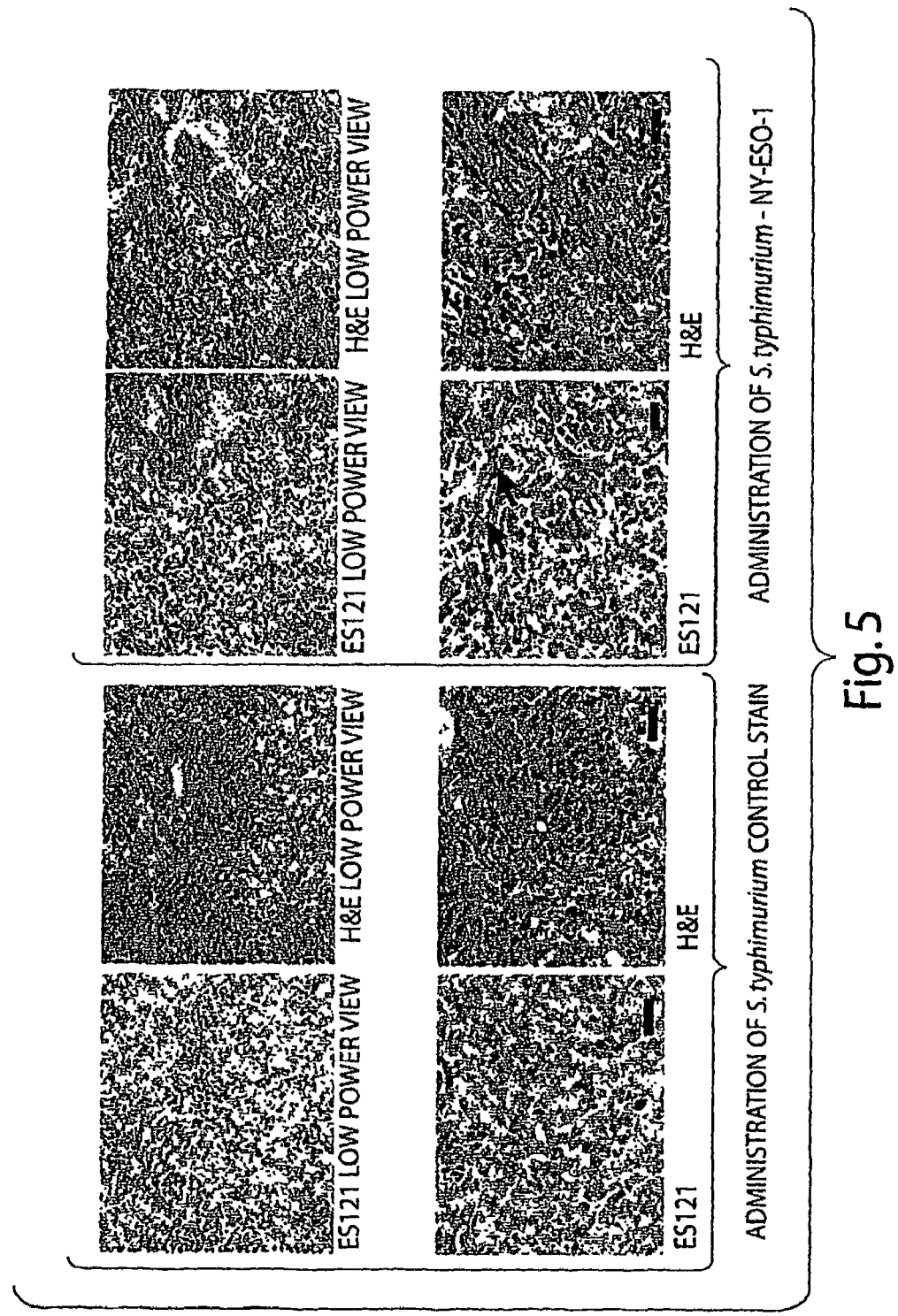

SEQUENCE LISTING

<160> NUMBER OF SEQ ID NOS: 2

<210> SEQ ID NO 1
<211> LENGTH: 30
<212> TYPE: PRT
<213> ORGANISM: Homo sapiens

<400> SEQUENCE: 1

```
Gly Ala Arg Gly Pro Glu Ser Arg Leu Leu Glu Phe Tyr Leu Ala Met
1               5                   10                  15

Pro Phe Ala Thr Pro Met Glu Ala Glu Leu Ala Arg Arg Ser
            20                  25                  30
```

<210> SEQ ID NO 2
<211> LENGTH: 24
<212> TYPE: PRT
<213> ORGANISM: Influenza virus

<400> SEQUENCE: 2

```
Phe Trp Arg Gly Glu Asn Gly Arg Lys Thr Arg Ile Ala Tyr Glu Arg
1               5                   10                  15

Met Cys Asn Ile Leu Lys Gly Lys
            20
```

METHODS FOR STIMULATING AN IMMUNE RESPONSE USING BACTERIAL ANTIGEN DELIVERY SYSTEM

RELATED APPLICATIONS

This application is a national stage filing under 35 U.S.C. §371 of international application PCT/US2006/038804, filed Oct. 3, 2006, which was published under PCT Article 21(2) in English, and claims the benefit under 35 U.S.C. §119(e) of U.S. provisional patent application Ser. No. 60/723,573, filed Oct. 4, 2005, the contents of which are incorporated herein by reference in their entirety.

GOVERNMENT SUPPORT

This invention was made with government support under Grant No. AI046953 awarded by the National Institutes of Health. The government has certain rights in the invention.

FIELD OF THE INVENTION

The invention relates to the use of the type III secretion system of bacteria to stimulate immune responses against tumor antigen(s), including for treating antigen-loss variant tumors. The invention also relates to preparing antigen presenting cells from peripheral blood mononuclear cells using bacteria having a type III secretion system.

BACKGROUND OF THE INVENTION

With the molecular identification of tumor specific antigens, a number of cancer vaccine trials targeting these antigens in the form of synthetic peptide epitopes have been attempted. Specific immune responses were observed in some clinical trials, however, only a minority of treated patients experienced clinical responses. Because of the weak clinical effectiveness of current cancer vaccine trials, many investigators are trying to discover more immunogenic antigens, new effective adjuvants, formulations, vectors or vaccination methods (Jager, E., et al., *Int. J. Cancer.* 106:817-20, 2003; Belardelli, F., et al., *Cancer Res.* 64:6827-30, 2004; Rosenberg, S. A., et al., *Nat. Med.* 10:909-15, 2004). Another obstacle for cancer vaccine trials is that patient enrollment is often limited by the indispensable requirement for antigen expression in cancer cells. Most attractive tumor specific antigens discovered so far have only a limited expression frequency in cancer, thus preventing many patients to meet adequate eligibility criteria.

NY-ESO-1 is a germ cell protein that is often expressed by cancer cells, but not normal somatic cells (Chen, Y. T. et al., *Proc. Natl. Acad. Sci. USA.* 94:1914-8, 1997). It was discovered by serological identification of antigens by recombinant expression cloning (SEREX) using the serum of an esophageal cancer patient (Chen, Y. T. et al., *Proc. Natl. Acad. Sci. USA.* 94:1914-8, 1997; Sahin, U. et al., *Proc. Natl. Acad. Sci. USA.* 92:11810-3, 1995). The frequent finding of humoral and cellular immune responses against this antigen in cancer patients with NY-ESO-1 expressing tumors makes it one of the most immunogenic human tumor antigens (Jager, E. et al., *J. Exp. Med.* 187:265-70, 1998). However, the frequency of NY-ESO-1 expression in melanoma, lung, breast, ovarian, and bladder cancers is only 20-30% and often heterogeneous (Chen, Y. T. et al., *Proc. Natl. Acad. Sci. USA.* 94: 1914-8, 1997; Jungbluth, A. A. et al., *Int. J. Cancer.* 92:856-60, 2001).

Although advances in the treatment of cancer have been made, there still exists a need for improved methods of treating cancer. In particular, there exists a need for improved cancer vaccines that can be used therapeutically and/or prophylactically.

SUMMARY OF THE INVENTION

Recent reports found that toll like receptor signals were important not only for eliciting immune responses but also for blocking suppressive activity by regulatory T cells, and recombinant viral and bacterial vectors have attracted attention for potentially providing necessary danger signals in vaccine vectors (Belardelli, F., et al., *Cancer Res.* 64:6827-30, 2004; Rosenberg, S. A., et al., *Nat. Med.* 10:909-15, 2004; Pasare, C. & Medzhitov, R., *Science.* 299:1033-6, 2003; Yang, Y., et al., *Nat. Immunol.* 5:508-15, 2004). One of the most promising candidates among bacterial vectors is *Salmonella enterica* serovar Typhimurium (*S. typhimurium*) (Russmann, H. et al., *Science.* 281:565-8, 1998; Shams, H., et al., *Vaccine.* 20:577-85, 2001; Evans, D. T. et al., *J. Virol.* 77:2400-9, 2003). The simplicity of its administration, the ease of its genetic manipulation, and the availability of several virulence-attenuating mutations have made *S. typhimurium* a very versatile antigen delivery platform (Galán, J. E. et al., *Gene* 94:29-35, 1990; Russman et al., 1998). Contact of *Salmonella typhimurium* with host cells causes activation of specialized protein secretion system, termed type III, that delivers a set of bacterial cytosolic proteins to the host cell cytosol without requiring bacterial uptake by target cells (Russmann, H. et al., *Science.* 281: 565-8, 1998; Stebbins, C. E. & Galan, J. E., *Nature.* 414:77-81, 2001; U.S. Pat. No. 6,306,387).

To use this unique protein secretion system, we established an avirulent construct, ΔphoP-phoQ *Salmonella typhimurium* recombinant for full-length NY-ESO-1 fused to the bacterial protein SopE bearing the type III secretion signal (Sal-NY-ESO-1). This construct has the potential to deliver NY-ESO-1 protein to the antigen presenting pathway of host professional and non-professional antigen presenting cells (APC) and thereby elicits immune responses. Such approach has proved efficient for priming CD8$^+$ T cells in models with *Salmonella typhimurium* expressing a lymphocytic choriomeningitis MHC class I-restricted epitope or simian immunodeficiency virus gag protein (Russmann, H. et al., *Science.* 281:565-8, 1998; Shams, H., et al., *Vaccine.* 20:577-85, 2001; Evans, D. T. et al., *J. Virol.* 77: 2400-9, 2003).

As noted above, there exists a need for improved cancer vaccines and the present invention addresses this need by providing methods for treating cancer using avirulent bacteria having a type III secretion system to deliver an antigen to a cell.

As proof of principle, we have engineered a recombinant *Salmonella typhimurium* construct that uses a specialized type III secretion system to inject NY-ESO-1 protein produced in the bacteria into host cells. We have examined its capacity to elicit in vitro NY-ESO-1-specific CD8$^+$ and CD4$^+$ T cell in humans, its in vivo treatment efficacy against NY-ESO-1 expressing tumors in mice, and its capacity to deliver antigen to the tumor cells in vivo.

We have found that *S. typhimurium*-NY-ESO-1 efficiently elicited NY-ESO-1-specific CD8$^+$ and CD4$^+$ T cell response in human PBMC derived from cancer patients with preexisting immunity in vitro. Furthermore, oral administration of *S. typhimurium*-NY-ESO-1 to mice resulted in the regression of pre-established NY-ESO-1 expressing tumors. Remarkably, administration of *S. typhimurium*-NY-ESO-1 at the local site of NY-ESO-1-negative tumors in the presence of preexisting NY-ESO-1-specific CD8$^+$ T cells, also led to tumor regression. Animals that showed tumor regression developed a CD8+ response not only to NY-ESO-1 but also to tumor antigens not contained in the vaccine i.e., through epitope spreading.

In aspects of the invention, methods for stimulating an immune response against a first protein expressed by a tumor are provided. The methods include administering to a subject in need of such treatment avirulent bacteria including a type III secretion system and a nucleic acid encoding a fusion protein that includes an immunogenic second protein expressed by the tumor or an immunogenic fragment thereof fused to a polypeptide that is delivered by the type III secretion system of the avirulent bacteria, where the fusion protein stimulates an immune response against the first protein and the immunogenic second protein. In some embodiments, the immune response is a CD8+ T cell response. In some embodiments, the immune response is a CD4+ T cell response. In some embodiments, the immune response is a CD8+ T cell response and a CD4+ T cell response. In certain embodiments, the immunogenic second protein or immunogenic fragment is a tumor antigen protein or an immunogenic fragment thereof.

In some embodiments, the avirulent bacteria are *Salmonella* spp., *Yersinia* spp., *Bordetella* spp., *Escherichia coli*, *Shigella* spp., *Burkholderia mallei, Burkholderia pseudomallei* or *Pseudomonas aeruginosa*. In certain embodiments, the avirulent bacteria are *Salmonella enterica*. In some embodiments, the avirulent *S. enterica* bacteria are *S. typhimurium*. In some embodiments, the avirulent bacteria are *S. typhimurium* pSB2470.

In some embodiments, more than one tumor antigen is encoded. In certain embodiments, the stimulation of the immune response is an increased pre-existing immune response. In some embodiments, the immune response comprises a CD8+ T cell response. In certain embodiments, the immune response comprises a CD4+ T cell response. In some embodiments, the immune response comprises a CD8+ T cell response and a CD4+ T cell response. In some embodiments, the second immunogenic protein or immunogenic fragment is a tumor antigen protein or an immunogenic fragment thereof.

In some embodiments, the avirulent bacteria are *Salmonella* spp., *Yersinia* spp., *Bordetella* spp., *Escherichia coli*, *Shigella* spp., *Burkholderia mallei, Burkholderia pseudomallei* or *Pseudomonas aeruginosa*. In some embodiments, the avirulent bacteria are *Salmonella enterica*. In certain embodiments, the avirulent *S. enterica* bacteria are *S. typhimurium*. In some embodiments, the avirulent *S. typhimurium* bacteria are *S. typhimurium* pSB2470. In some embodiments, more than one tumor antigen is encoded.

In aspects of the invention, methods for stimulating an immune response against a first protein expressed by a tumor are provided. The methods include administering to a subject in need of such treatment a nucleic acid that expresses an immunogenic second protein or an immunogenic fragment thereof, and administering subsequently to the subject avirulent bacteria including a type III secretion system and a nucleic acid encoding a fusion protein that includes the immunogenic second protein or immunogenic fragment thereof fused to a polypeptide that is delivered by the type III secretion system of the avirulent bacteria. In certain embodiments, the immune response is a CD4+ T cell response. In some embodiments, the immune response is a CD8+ T cell response. In some embodiments, the immune response is a both a CD4+ T cell response and a CD8+ T cell response. In certain embodiments, the second immunogenic protein or immunogenic fragment is a tumor antigen protein or an immunogenic fragment thereof.

In some embodiments, the avirulent bacteria are *Salmonella* spp., *Yersinia* spp., *Bordetella* spp., *Escherichia coli*, *Shigella* spp., *Burkholderia mallei, Burkholderia pseudomallei* or *Pseudomonas aeruginosa*. In certain embodiments, the avirulent bacteria are *Salmonella enterica*. In some embodiments, the avirulent *S. enterica* bacteria are *S. typhimurium*. In some embodiments, the avirulent *S. typhimurium* bacteria are *S. typhimurium* pSB2470.

In some embodiments, the avirulent bacteria are administered orally. In certain embodiments, the nucleic acid is administered parenterally. In some embodiments, more than one tumor antigen is encoded. In some embodiments, the stimulation of the immune response is an increased pre-existing immune response. In certain embodiments, the immune response includes a CD4+ T cell response. In some embodiments, the immune response comprises a CD8+ T cell response. In some embodiments, the immune response comprises a CD4+ T cell response and a CD8+ T cell response.

In some embodiments, the second immunogenic protein or immunogenic fragment is a second tumor antigen protein or an immunogenic fragment thereof. In some embodiments, the avirulent bacteria are *Salmonella* spp., *Yersinia* spp., *Bordetella* spp., *Escherichia coli, Shigella* spp., *Burkholderia mallei, Burkholderia pseudomallei* or *Pseudomonas aeruginosa*. In another embodiment, the avirulent bacteria are *Salmonella enterica*. In certain embodiments, the avirulent *S. enterica* bacteria are *S. typhimurium*. In some embodiments, the avirulent *S. typhimurium* bacteria are *S. typhimurium* pSB2470.

In some embodiments, the avirulent bacteria are administered orally. In some embodiments, the nucleic acid is administered parenterally. In certain embodiments, more than one tumor antigen is encoded.

In aspects of the invention, methods for inducing an immune response to a tumor are provided. The methods include administering, to a subject having a tumor, a recombinant avirulent bacteria includes a type III secretion system that expresses by the type III secretion system an antigen to which the subject has a pre-existing immune response, whereby at least some of the cells of the tumor express the antigen. In a second embodiment, the second immunogenic protein or immunogenic fragment is a tumor antigen protein of an immunogenic fragment thereof.

In some embodiments, the avirulent bacteria are *Salmonella* spp., *Yersinia* spp., *Bordetella* spp., *Escherichia coli, Shigella* spp., *Burkholderia mallei, Burkholderia pseudomallei* or *Pseudomonas aeruginosa*. In some embodiments, the avirulent bacteria are *Salmonella enterica*. In another embodiment, the avirulent *S. enterica* bacteria are *S. typhimurium*. In certain embodiments, the avirulent *S. typhimurium* bacteria are *S. typhimurium* pSB2470.

In some embodiments, the recombinant avirulent bacteria are administered intratumorally. In some embodiments, the recombinant avirulent bacteria are administered by injection. In certain embodiments, the recombinant avirulent bacteria are administered to the site of the tumor. In some embodiments, the recombinant avirulent bacteria are administered after resection of all or part of the tumor.

In some embodiments, the antigen is an antigen of a virus. In some embodiments, the virus is an influenza virus, an Epstein-Barr virus or a Varicella zoster virus. In certain embodiments, the antigen is an antigen of a microorganism against which the subject has been immunized. In some embodiments, the microorganism causes mumps, measles, rubella, chicken pox, influenza, diphtheria, tetanus, pertussis, hepatitis A, hepatitis B, bacterial meningitis (*Haemophilus influenzae* type b), polio or *Streptococcus pneumoniae* infection (invasive pneumococcal disease). In some embodiments, the antigen is an non-tumor antigen. In certain embodiments, the antigen is a tumor antigen. In some embodiments, the tumor antigen is NY-ESO-1, a MAGE antigen, a SSX antigen, SCP1, CT7, NY-CO-58, a BAGE antigen, a GAGE antigen, Melan-A/MART-1, gp100 or gp75. In certain embodiments, the tumor antigen is NY-ESO-1. In certain embodiments, the tumor antigen is NY-CO-58. In some embodiments, the tumor antigen is MAGE-A3. In some embodiments, the tumor antigen is SSX2. In some embodiments, the expression of antigen in the cells is sufficient to induce cross-presentation to bone marrow-derived stromal cells. In some embodiments, more than one tumor antigen is encoded.

In aspects of the invention, methods for treating antigen-loss variant tumors in a subject are provided. The methods include administering to one or more antigen-loss variant tumors a recombinant avirulent bacteria including a type III secretion system that expresses by the type III secretion system an antigen, the expression of which is lost in the one or more antigen-loss variant tumors, where the recombinant avirulent bacteria infects the cells of the one or more antigen loss variant tumors and causes expression of the antigen in the cells, thereby inducing an immune response against the one or more antigen loss variant tumors. In some embodiments, the second immunogenic protein or immunogenic fragment is a tumor antigen protein or an immunogenic fragment thereof.

In some embodiments, the avirulent bacteria are *Salmonella* spp., *Yersinia* spp., *Bordetella* spp., *Escherichia coli*, *Shigella* spp., *Burkholderia mallei*, *Burkholderia pseudomallei* or *Pseudomonas aeruginosa*. In some embodiments, the avirulent bacteria are *Salmonella enterica*. In certain embodiments, the avirulent *S. enterica* bacteria are *S. typhimurium*. In some embodiments, the avirulent *S. typhimurium* bacteria are *S. typhimurium* pSB2470.

In some embodiments, the recombinant avirulent bacteria are administered intratumorally. In some embodiments, the recombinant avirulent bacteria are administered by injection. In some embodiments, the recombinant avirulent bacteria are administered to the site of the tumor. In certain embodiments, the recombinant avirulent bacteria are administered after resection of all or part of the tumor.

In some embodiments, the administration induces a CD4+ immune response. In some embodiments, the administration induces a CD8+ immune response. In some embodiments, the expression of antigen in the cells is sufficient to induce cross-presentation to bone marrow-derived stromal cells. In certain embodiments, the antigen is a tumor antigen. In some embodiments, the tumor antigen is NY-ESO-1, a MAGE antigen, a SSX antigen, SCP1, CT7, NY-CO-58, a BAGE antigen, a GAGE antigen, Melan-A/MART-1, gp100 or gp75. In some embodiments, the tumor antigen is NY-ESO-1. In some embodiments, the tumor antigen is NY-CO-58. In certain embodiments, the tumor antigen is MAGE-A3. In some embodiments, the tumor antigen is SSX2. In some embodiments, more than one tumor antigen is encoded.

In aspects of the invention, methods for preparing antigen presenting cells from peripheral blood mononuclear cells are provided. The methods include obtaining peripheral blood mononuclear cells (PBMCs) from a subject, contacting the PBMCs with a recombinant avirulent bacteria including a type III secretion system that expresses by the type III secretion system an antigen, culturing the contacted PBMCs, and isolating antigen presenting cells. In some embodiments, the PBMCs are CD4− CD8− PBMCs.

In some embodiments, the avirulent bacteria are *Salmonella* spp., *Yersinia* spp., *Bordetella* spp., *Escherichia coli*, *Shigella* spp., *Burkholderia mallei*, *Burkholderia pseudomallei* or *Pseudomonas aeruginosa*. In some embodiments, the avirulent bacteria are *Salmonella enterica*. In certain embodiments, the avirulent *S. enterica* bacteria are *S. typhimurium*. In some embodiments, the avirulent *S. typhimurium* bacteria are *S. typhimurium* pSB2470.

In some embodiments, the antigen is a tumor antigen. In some embodiments, the tumor antigen is NY-ESO-1, a MAGE antigen, a SSX antigen, SCP1, CT7, NY-CO-58, a BAGE antigen, a GAGE antigen, Melan-A/MART-1, gp100 or gp75. In certain embodiments, the tumor antigen is NY-ESO-1. In some embodiments, the tumor antigen is NY-CO-58. In some embodiments, the tumor antigen is MAGE-A3. In yet another embodiment, the tumor antigen is SSX2.

In aspects of the invention, an isolated population of antigen presenting cells prepared by any method of the invention is provided. In some embodiments, the cells are antigen presenting cells.

In aspects of the invention, methods for preparing antigen-specific T cells are provided. The methods include obtaining peripheral blood mononuclear cells (PBMCs) from a subject, contacting the PBMCs with the antigen presenting cells of the invention, culturing the contacted PBMCs, and isolating antigen-specific T cells from the PBMCs. In some embodiments, the antigen-specific T cells are CD4+ T cells. In certain embodiments, the antigen-specific T cells are CD8+ T cells.

In aspects of the invention, an isolated population of antigen-specific T cells prepared by any method of the invention are provided. In some embodiments, the isolated population of antigen-specific T cells are CD4+ T cells. In certain embodiments, the isolated population of antigen-specific T cells are CD8+ T cells.

In aspects of the invention, methods for passive immunization are provided. The methods include administering to a subject in need of such treatment a population of T cells as prepared by any method of the invention.

In aspects of the invention, kits for immunization are provided. The kits include a first container containing a DNA vaccine vector encoding an antigen and a second container containing recombinant avirulent bacteria including a type III secretion system that expresses by the type III secretion system the antigen. In some embodiments, the antigen is a tumor antigen. In some embodiments, the tumor antigen is NY-ESO-1, a MAGE antigen, a SSX antigen, SCP1, CT7, NY-CO-58, a BAGE antigen, a GAGE antigen, Melan-A/MART-1, gp100 or gp75. In some embodiments, the tumor antigen is NY-ESO-1. In some embodiments, the tumor antigen is NY-CO-58. In some embodiments, the tumor antigen is MAGE-A3. In some embodiments, the tumor antigen is SSX2.

In aspects of the invention, kits for immunization are provided. The kits include a first container containing one or more doses of a vaccine against an antigen and a second container containing a recombinant avirulent bacteria including a type III secretion system that expresses by the type III secretion system the antigen. In some embodiments, the antigen is not a tumor antigen. In some embodiments, the antigen causes mumps, measles, rubella, chicken pox, influenza, diphtheria, tetanus, pertussis, hepatitis A, hepatitis B, bacterial meningitis (*Haemophilus influenzae* type b), polio or *Streptococcus pneumoniae* infection (invasive pneumococcal disease). In certain embodiments, the antigen is a tumor antigen. In some embodiments, the tumor antigen is NY-ESO-1, a MAGE antigen, a SSX antigen, SCP1, CT7, NY-CO-58, a BAGE antigen, a GAGE antigen, Melan-A/MART-1, gp100 or gp75. In some embodiments, the tumor antigen is NY-ESO-1. In some embodiments, the tumor antigen is NY-CO-58. In some embodiments, the tumor antigen is MAGE-A3. In certain embodiments, the tumor antigen is SSX2.

In aspects of the invention, an avirulent recombinant bacteria including a nucleic acid that encodes a fusion protein consisting of NY-ESO-1 or an immunogenic fragment thereof fused to a polypeptide that is delivered by the type III secretion system of the avirulent bacteria is provided. In some embodiments, the avirulent bacteria is Salmonella spp., Yersinia spp., Bordetella spp., Escherichia coli, Shigella spp., Burkholderia mallei, Burkholderia pseudomallei or Pseudomonas aeruginosa. In some embodiments, the avirulent bacteria are Salmonella enterica. In certain embodiments, the avirulent Salmonella enterica bacteria are S. typhimurium. In some embodiments, the avirulent S. typhimurium bacteria are S. typhimurium pSB2470.

In aspects of the invention, an avirulent recombinant bacteria including a nucleic acid that encodes a fusion protein consisting of NY-CO-58 or an immunogenic fragment thereof fused to a polypeptide that is delivered by the type III secretion system of the avirulent bacteria is provided. In some embodiments, the avirulent bacteria are Salmonella spp., Yersinia spp., Bordetella spp., Escherichia coli, Shigella spp., Burkholderia mallei, Burkholderia pseudomallei or Pseudomonas aeruginosa. In certain embodiments, the avirulent bacteria are Salmonella enterica. In a some embodiments, the avirulent Salmonella enterica bacteria are S. typhimurium. In some embodiments, the avirulent S. typhimurium bacteria are S. typhimurium pSB2470.

The use of the foregoing compositions in the preparation of medicament also is provided. In preferred embodiments, the medicament is useful in the treatment of cancer.

These and other objects of the invention will be described in further detail in connection with the detailed description of the invention.

BRIEF DESCRIPTION OF THE DRAWINGS

FIG. 1. S. typhimurium type III secretion system delivers recombinant NY-ESO-1 to target cells

FIG. 2. Antigens delivered by the S. typhimurium type III secretion are efficiently presented to CD8$^+$ T cells

FIG. 3. S. typhimurium type III secretion system induces antigen-specific primary CD8$^+$ T cells from PBMC FIG. 3a: CD8$^+$ T cells derived from PBMC of NW29 and NW634 were pre-sensitized by CD4$^-$ CD8$^-$ PBMC infected with S. typhimurium-NY-ESO-1 or S. typhimurium control strain and induction of specific CD8$^+$ T cells was analyzed by ELISPOT assay for recognition of autologous EBV-B cells pulsed with peptides or infected with recombinant Fowlpox virus. Data are expressed as mean±SD.

FIG. 3b: NY-ESO-1-specific CD8$^+$ T cells induced from NW29 were stained with NY-ESO-1$_{92-100}$/HLA-Cw*0304 tetramer-PE and anti-CD8-Tricolor and analyzed by flow cytometry. These experiments were performed independently at least twice with similar results.

FIG. 4. Oral administration of S. typhimurium-NY-ESO-1 causes tumor regression in mice bearing NY-ESO-1 positive tumors

FIG. 5. Intratumoral administration of S. typhimurium results in the delivery of antigen at the tumor site BALB/c mice were inoculated with 1×10$^6$ parental CMS5a. One week later, 0.5-1×10$^6$ S. typhimurium-NY-ESO-1 or S. typhimurium control strain were directly inoculated to palpable tumors. After surgical removal, the presence of NY-ESO-1 at the tumor site was examined by immunohistochemistry as described in Methods. Arrows indicate NY-ESO-1 positive cells. Scale bar=1 μm.

FIG. 6. Local tumor antigen delivery by S. typhimurium type III secretion causes regression of tumors in mice by epitope spreading

FIG. 8 shows a schematic diagram of *S. typhimurium* vaccine construct expressing the tumor antigen NY-CO-58 fused to the secretion and translocation signals of SopE. Also depicted is a protein gel showing expression of this construct in the whole cell lysate and supernatant fraction.

DESCRIPTION OF SEQUENCES

Figure 1A:
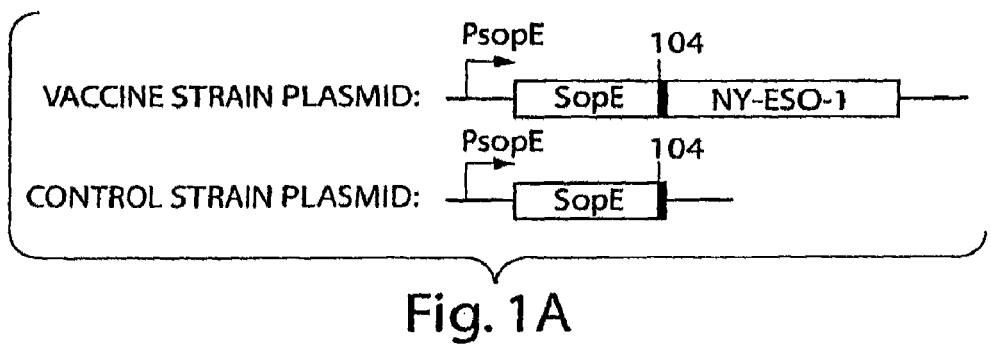
FIG. 1a: Diagram of relevant plasmids used in these studies.

SEQ ID NO:1—Amino acid sequence of synthetic peptide of NY-ESO-$1_{79-108}$.
SEQ ID NO:2—Amino acid sequence of synthetic peptide of influenza $NP_{206-229}$.

DETAILED DESCRIPTION OF THE INVENTION

*Salmonella* species have the ability to stimulate potent inflammatory responses, which is the consequence of their ability to directly stimulate the innate immune system. It is this property that makes *Salmonella* an effective antigen delivery system, given the demonstrated importance of the innate immune system in the generation of acquired immune responses. The benefits of the stimulation of innate immune and inflammatory responses within the tumor itself for the generation of specific immune responses to tumor antigens is well documented (Finn, O. J., et al., *Nat Rev Immunol.*, 3:630-41, 2003; Gilboa, E., *Nat Rev Cancer*, 4:401-411, 2004).

As noted above, the type III section system of certain bacteria, e.g., *Salmonella typhimurium*, is activated upon contact of the bacteria with host cells. The type III secretion system delivers a set of bacterial cytosolic proteins to the host cell cytosol without requiring bacterial uptake by the cells. To demonstrate the use of this unique protein secretion system for stimulating immune responses, particularly immune responses against tumor antigens, we established avirulent bacterial constructs, ΔphoP-phoQ *Salmonella typhimurium* recombinant for antigens fused to the bacterial protein SopE bearing the type III secretion signal (e.g., SopE fused to the full-length tumor antigen NY-ESO-1). These constructs have the potential to deliver antigen proteins to the antigen presenting pathway of host professional and non-professional antigen presenting cells (APCs) and thereby elicit or increase immune responses.

A bacterial type III secretion system involves the secretion and delivery of bacterial effector proteins into the cytosol of a host cell, without requiring the uptake of the bacteria. The type III secretion system results in delivery of one or more antigens to antigen-presenting pathways, potentially involving both Class I- and Class II-restricted pathways. Any type III secretion systems known to exist and yet to be discovered are examples of "type III secretion systems" in accordance with the subject invention. For example, currently known targets of bacterial type III secretion systems include the SptP, SipA, SipB, SipC, SipD, InvJ, SpaO, AvrA, and SopE proteins of *Salmonella*, the Yop and Ypk proteins of *Yersinia* (for example, YopE, YopH, YopM and YpkA), the Ipa proteins of *Shigella*, and the ExoS proteins of *Pseudomonas aeruginosa*.

In certain aspects of the invention, methods for stimulating an immune response against a tumor antigen are provided. Immune responses are well known to those of ordinary skill in the art, and it is contemplated that an immune response can be a cell mediated response and/or an antibody response. The immune responses stimulated in accordance with the invention include Th1 responses, Th2 responses, or mixed Th1/Th2 responses. Accordingly, the stimulated immune response can be a CD8+ T cell response, a CD4+ T cell response or both a CD8+ T cell response and a CD4+ T cell response. In some embodiments, stimulation of an immune response includes stimulation of a pre-existing immune response that existed through previous exposure to antigen.

An "antigen", as used herein, is a substance that stimulates a specific immune response; for the purposes of this invention, antigens include both tumor antigens and non-tumor antigens. Antigens encoded and delivered by the avirulent recombinant bacteria of the invention are polypeptides.

Non-tumor antigens include without limitation virus antigens and antigens of a microorganism. Viral antigens include, but are not limited to, antigens of: influenza virus, Epstein-Barr virus and Varicella zoster virus. Viral antigens also include antigens of viruses that cause viral diseases, including: mumps, measles, rubella, chicken pox, influenza, hepatitis A, hepatitis B and polio. Antigens of a microorganism include, but are not limited to, antigens of microorganisms that cause diphtheria, tetanus, pertussis, bacterial meningitis (*Haemophilus influenza* type B), and *Streptococcus pneumoniae* antigen (invasive pneumococcal disease).

A tumor antigen as used herein refers to tumor antigen polypeptides, which includes tumor antigen proteins or fragments thereof, and tumor antigen peptides. Preferred tumor antigens include, but are not limited to: NY-ESO-1, a MAGE antigen, for example MAGE-A3, a SSX antigen, for example SSX2, SCP1, CT7, NY-CO-58, a BAGE antigen, a GAGE antigen, Melan-A/MART-1, gp100 and gp75. Cancer-testis antigens, which are expressed only or primarily in cancer cells and testis cells, are preferred tumor antigens. A list of some cancer-testis antigens is provided in Table 1 (Cancer Immunity, 4:1 (2004) Table 1).

TABLE 1

| Current list of CT genes: 44 CT gene families, 89 individual genes or isoforms | | |
| --- | --- | --- |
| Transcript/ Transcript family | CT Identifier | Family Members/CT Identifier |
| MAGEA | CT1 | MAGEA1/CT1.1, MAGEA2/CT1.2, MAGEA3/CT1.3, MAGEA4/CT1.4, MAGEA5/CT1.5, MAGEA6/CT1.6, MAGEA7/CT1.7, MAGEA8/CT1.8, MAGEA9/CT.9, MAGEA10/CT1.10, MAGEA11/CT1.11, MAGEA12/CT1.12 |

TABLE 1-continued

Current list of CT genes: 44 CT gene families,
89 individual genes or isoforms

| Transcript/ Transcript family | CT Identifier | Family Members/CT Identifier |
|---|---|---|
| BAGE | CT2 | BAGE/CT2.1, BAGE2/CT2.2, BAGE3/CT2.3, BAGE4/CT2.4, BAGE5/CT2.5 |
| MAGEB | CT3 | MAGEB1/CT3.1, MAGEB2/CT3.2, MAGEB5/CT3.3, MAGEB6/CT3.4 |
| GAGE1 | CT4 | GAGE1/CT4.1, GAGE2/CT4.2, GAGE3/CT4.3, GAGE4/CT4.4, GAGE5/CT4.5, GAGE6/CT4.6, GAGE7/CT4.7, GAGE8/CT4.8 |
| SSX | CT5 | SSX1/CT5.1, SSX2/CT5.2a, SSX2/CT5.2b, SSX3/CT5.3, SSX4/CT5.4 |
| NY-ESO-1 | CT6 | NY-ESO-1/CT6.1, LAGE-1a/CT6.2a, LAGE-1b/CT6.2b |
| MAGEC1 | CT7 | MAGEC1/CT7.1, MAGEC3/CT7.2 |
| SYCP1 | CT8 | SYCP1/CT8 |
| BRDT | CT9 | BRDT/CT9 |
| MAGEE1 | CT10 | MAGEE1/CT10 |
| CTp11/SPANX | CT11 | SPANXA1/CT11.1, SPANXB1/CT11.2, SPANXC/CT11.3, SPANXD/CT11.4 |
| XAGE-1/GAGED | CT12 | XAGE-1a/CT12.1a, XAGE-1b/CT12.1b, XAGE-1c/CT12.1c, XAGE-1d/CT12.1d, XAGE-2/CT12.2, XAGE-3a/CT12.3a, XAGE-3b/CT12.3b, XAGE-4/CT12.4 |
| HAGE | CT13 | HAGE/CT13 |
| SAGE | CT14 | SAGE/CT14 |
| ADAM2 | CT15 | ADAM2/CT15 |
| PAGE-5 | CT16 | PAGE-5/CT16.1, CT16.2 |
| LIP1 | CT17 | LIP1/CT17 |
| NA88 | CT18 | NA88/CT12 |
| IL13RA1 | CT19 | IL13RA1/CT19 |
| TSP50 | CT20 | TSP50/CT20 |
| CTAGE-1 | CT21 | CTAGE-1/CT21.1, CTAGE-2/CT21.2 |
| SPA17 | CT22 | SPA17/CT22 |
| OY-TES-1 | CT23 | OY-TES-1/CT23 |
| CSAGE | CT24 | CSAGE/CT24.1, TRAG3/CT24.2 |
| MMA1/DSCR8 | CT25 | MMA-1a/CT25.1a, MMA-1b/CT25.1b |
| CAGE | CT26 | CAGE/CT26 |
| BORIS | CT27 | BORIS/CT27 |
| HOM-TES-85 | CT28 | HOM-TES-85/CT28 |
| AF15q14/D40 | CT29 | D40/CT29 |
| E2F-like/HCA661 | CT30 | HCA661/CT30 |
| PLU-1 | CT31 | PLU-1/CT31 |
| LDHC | CT32 | LDHC/CT32 |
| MORC | CT33 | MORC/CT33 |
| SGY-1 | CT34 | SGY-1/CT34 |
| SPO11 | CT35 | SPO11/CT35 |
| TPX1 | CT36 | TPX-1/CT36 |
| NY-SAR-35 | CT37 | NY-SAR-35/CT37 |
| FTHL17 | CT38 | FTHL17/CT38 |
| NXF2 | CT39 | NXF2/CT39 |
| TAF7L | CT40 | TAF7L/CT40 |
| TDRD1 | CT41 | TDRD1/CT41.1, NY-CO-45/CT41.2 |
| TEX15 | CT42 | TEX15/CT42 |
| FATE | CT43 | FATE/CT43 |
| TPTE | CT44 | TPTE/CT44 |

Other aspects of the invention provide methods for expressing a polypeptide as described herein, using avirulent bacteria. In exemplary embodiments the avirulent bacteria include a type III secretion system. Such bacteria are known to those of ordinary skill in the art. Briefly, such bacteria provide delivery of proteins to a cell cytosol without the requirement of the bacteria entering the target cell. Further details can be found in Russmann, H. et al., *Science*, 281:565-8, 1998; Stebbins, C. E. et al., *Nature*, 414:77-81, 2001. Bacteria with Type III secretion systems include but are not limited to *Salmonella* spp., *Yersinia* spp., *Bordetella* spp., *Escherichia coli*, *Shigella* spp., *Burkholderia mallei*, *Burkholderia pseudomallei*, and *Pseudomonas aeruginosa*. In a preferred embodiment, an avirulent bacteria is *Salmonella typhimurium*. In particularly preferred embodiment, an avirulent bacteria is ΔphoP-phoQ *Salmonella typhimurium*. In a specific embodiment, an avirulent bacteria is *Salmonella typhimurium* pSB2470, described in Russmann et al. 1998. *Science*. 281:565-568.

Avirulent bacteria are grown and maintained in sterile media under bacterial growth conditions as known to those of ordinary skill in the art. In some instances the avirulent bacteria may contain a deletion in the asd gene encoding aspartate semialdehyde dehydrogenase involved in the synthesis of diaminopimelic acid (DAP), an essential component of the peptidoglycan layer of the bacterial envelope. Bacteria lacking the asd gene can only grow in medium containing DAP. It is contemplated that the avirulent bacteria in these instances are grown in the presence of diaminopimelic acid (DAP) to aid replication. Mammals do not produce DAP therefore bacteria lacking the asd gene are able to replicate for a limited number of generations, rendering the bacteria avirulent. The asd gene deletion removes the need for using antibiotics. The removal of the need for antibiotics ensures the vaccine complies with FDA regulations.

Methods for treating antigen-loss variant tumors are provided. As used herein, "antigen-loss variant" is a tumor or tumor cells that have reduced or eliminated the expression of a tumor antigen. By reducing or eliminating tumor antigen expression, antigen-loss variant tumors may evade detection and killing by the immune system, which otherwise would generate an immune response against these antigens expressed by the tumor cells. A recombinant avirulent bacteria having a type III secretion system that expresses an antigen is administered to a subject having reduced or no expression of the antigen (e.g. to an antigen-loss variant tumor in the subject). One or more antigens may be administered with the result that the absent antigen(s) is expressed in the subject stimulating an immune response. It is also contemplated that the expression of the absent antigen in the subject is sufficient to induce cross-presentation to bone marrow-derived stromal cells.

Cross-presentation is the process by which an antigen presenting cell, such as a dendritic cell, can display antigen on both MHC-I and MHC-II. The antigen presenting cell typically phagocytoses a virus-infected cell or a cancerous cell to obtain the antigen. The antigen is displayed on both MHC-I and MHC-II and the dendritic cell can induce a response from both CD8$^+$ cells (via MHC-I presentation) and CD4$^+$ cells (via MHC-II presentation). The dendritic cell releases co-stimulators that most non-immune cells do not express. These co-stimulators facilitate the activation and clonal proliferation of naive CD8$^+$ T-cells into cytolytic effector T-cells.

As used herein, a "nucleic acid molecules encoding" means the nucleic acid molecules that code for the antigen polypeptides or immunogenic fragments thereof. These nucleic acid molecules may be DNA or may be RNA (e.g. mRNA). The nucleic acid molecules encoding (tumor) antigen(s) also encompass variants of the nucleic acid molecules described herein. These variants may be splice variants or allelic variants of certain antigen-encoding sequences. Variants of the nucleic acid molecules of the invention are intended to include homologs and alleles which are described further below. Further, as used herein, the term "tumor antigen molecules" includes tumor antigens (polypeptides and fragments thereof) as well as tumor antigen nucleic acids. In all embodiments, human tumor antigens and the encoding nucleic acid molecules thereof are preferred.

In one aspect, the invention provides isolated nucleic acid molecules that encode the antigens for use in the methods and compositions described herein. Exemplary isolated nucleic acid molecules of the invention are: (a) nucleotide sequences encoding SEQ ID NO: 1 or fragments thereof (b) isolated nucleic acid molecules which hybridize under highly stringent conditions to the nucleic acid molecules of (a) and which code for a tumor antigen, (c) nucleic acid molecules that differ from (a) or (b) due to the degeneracy of the genetic code, and (d) complements of (a), (b) or (c). In certain preferred embodiments, the nucleic acid molecules are those that encode a polypeptide having an amino acid sequence as set forth in SEQ ID NO: 1, or an immunogenic fragment thereof, or nucleic acid molecules comprising a nucleotides sequence that is at least about 90% identical to a nucleotide sequence that encodes SEQ ID NO: 1.

As used herein the term "isolated nucleic acid molecule" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art.

The nucleic acid molecules of the invention that encode antigen(s) are also intended to encompass homologs and alleles which can be identified by conventional techniques as well as by in silico (i.e., computer-based homology screening using computer software). Identification of human homologs and homologs of other organisms (i.e., orthologs) of tumor antigen polypeptides will be familiar to those of skill in the art. In general, nucleic acid hybridization is a suitable method for identification of homologous sequences of another species which correspond to a known sequence. Standard nucleic acid hybridization procedures can be used to identify related nucleic acid sequences of selected percent identity. For example, one can construct a library of cDNAs reverse transcribed from the mRNA of a selected tissue and use the nucleic acids that encode selected tumor antigen(s), such as those identified herein, to screen the library for related nucleotide sequences. The screening preferably is performed using high-stringency conditions to identify those sequences that are closely related by sequence identity. Nucleic acids so identified can be translated into polypeptides and the polypeptides can be tested for activity.

The term "high stringency" as used herein refers to parameters with which the art is familiar. Nucleic acid hybridization parameters may be found in references that compile such methods, e.g., Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. More specifically, high-stringency conditions, as used herein, refers, for example, to hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$ (pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, the membrane upon which the DNA is transferred is washed, for example, in 2×SSC at room temperature and then at 0.1-0.5× SSC/0.1×SDS at temperatures up to 68° C. The temperature of the wash may be adjusted to provide different levels of stringency. For example the wash can be performed at temperatures of 42° C., 45° C., 50° C., 55° C., 60° C., 65° C. or 68° C. The skilled artisan would be able to adjust the conditions to determine the optimum conditions as required.

There are other conditions, reagents, and so forth that can be used, which result in a similar degree of stringency. The skilled artisan will be familiar with such conditions, and thus they are not given here. It will be understood, however, that the skilled artisan will be able to manipulate the conditions in a manner to permit the clear identification of homologs and alleles of the tumor antigen nucleic acids of the invention (e.g., by using lower stringency conditions). The skilled artisan also is familiar with the methodology for screening cells and libraries for expression of such molecules, which then are routinely isolated, followed by isolation of the pertinent nucleic acid molecule and sequencing.

Optimal alignment of sequences for comparison may alternatively be conducted using programs such as BLAST, publicly available on the National Library of Medicine website. Other programs such as UniGene (The National Library of Medicine website), SAGE Anatomic Reviewer and its Virtual Northern tool, (The Cancer Genome Anatomy Project CGAP website) are also publicly available. One of ordinary skill in the art would be able to use these programs to align sequences and determine percentage identity with no more than routine experimentation.

In general, homologs and alleles typically will share at least 90% nucleotide identity and/or at least 95% amino acid identity to the sequences of cancer-testis nucleic acids and polypeptides, respectively, in some instances will share at least 95% nucleotide identity and/or at least 97% amino acid identity, in other instances will share at least 97% nucleotide identity and/or at least 98% amino acid identity, in other instances will share at least 99% nucleotide identity and/or at least 99% amino acid identity, and in other instances will share at least 99.5% nucleotide identity and/or at least 99.5% amino acid identity. The homology can be calculated using various, publicly available software tools developed by NCBI (Bethesda, Md.) that can be obtained through the internet. Exemplary tools include the BLAST system available from the website of the National Center for Biotechnology Information (NCBI) at the National Institutes of Health. Pairwise and ClustalW alignments (BLOSUM30 matrix setting) as well as Kyte-Doolittle hydropathic analysis can be obtained using the MacVector sequence analysis software (Oxford Molecular Group). Watson-Crick complements of the foregoing nucleic acids also are embraced by the invention.

In another aspect of the invention, fragments are contemplated. A fragment includes but is not limited to a fragment of a nucleic acid or a fragment of a polypeptide molecule. In an embodiment a fragment is an immunogenic fragment. For polypeptides, the fragment can be at least about 5, 6, 7, 8, 9, 10, 11, 12, 13, 14, 15, 16, 17, 18, 19, 20, 25, 30, 35, 40, 45, 50, 75, or 100 amino acids in length. For nucleic acid molecules the fragment can be at least about 12, 13, 14, 15, 16, 17, 18, 19, 20, 21, 22, 23, 24, 25, 26, 27, 28, 29, 30, 31 and 32 bases long. In some embodiments a nucleic acid fragment can be at least about 35, 40, 45, 50, 55, 60, 65, 70, 75, 100, 150, 200, 250, 300, or 500 nucleotides in length.

In an exemplary embodiment of the invention the polypeptides are fusion proteins. In an embodiment the fusion protein consists of NY-ESO-1 or an immunogenic fragment thereof fused to a polypeptide that is secreted by a type III secretion system. Examples of such peptides include: SptP, SipA, SipB, SipC, SipD, InvJ, SpaO, AvrA, and SopE proteins of *Salmonella*, the Yop and Ypk proteins of *Yersinia* (for example, YopE, YopH, YopM and YpkA), the Ipa proteins of *Shigella*, and the ExoS proteins of *Pseudomonas aeruginosa*.

Fragments of the immunogenic tumor antigen polypeptides (including immunogenic peptides) also can be synthesized chemically using well-established methods of peptide synthesis. Thus, fragments of the disclosed polypeptides are useful for eliciting an immune response and for assaying for the presence of antibodies, or other similar molecules such as T cell receptors. In one embodiment fragments of a polypeptide which comprises SEQ ID NO: 1 or fragments thereof that are at least eight amino acids in length and exhibit immunogenicity are provided. The fragments may be any length from 8 amino acids up to one amino acid less than the full length size of polypeptide Specific embodiments provide fragments of a polypeptide which comprise the polypeptide sequences set forth as SEQ ID NO: 1 or the fragments described above.

Fragments of a polypeptide preferably are those fragments that retain a distinct functional capability of the polypeptide. Functional capabilities that can be retained in a fragment of a polypeptide include interaction with antibodies or MHC molecules (e.g. immunogenic fragments), interaction with other polypeptides or fragments thereof, selective binding of nucleic acids or proteins, and enzymatic activity. One important activity is the ability to provoke in a subject an immune response. As will be recognized by those skilled in the art, the size of the fragment that can be used for inducing an immune response will depend upon factors such as whether the epitope recognized by an antibody is a linear epitope or a conformational epitope or the particular MHC molecule that binds to and presents the fragment (e.g. HLA class I or II). Thus, some immunogenic fragments of tumor antigen polypeptides will consist of longer segments while others will consist of shorter segments, (e.g. about 8, 9, 10, 11, 12, 13, 14, 15, 16 or more amino acids long, including each integer up to the full length of the polypeptide). Those skilled in the art are well versed in methods for selecting immunogenic fragments of polypeptides.

The invention embraces variants of the tumor antigen polypeptides described above. As used herein, a "variant" of a tumor antigen polypeptide is a polypeptide which contains one or more modifications to the primary amino acid sequence of a tumor antigen polypeptide. Modifications which create a tumor antigen variant can be made to a tumor antigen polypeptide 1) to reduce or eliminate an activity of a tumor antigen polypeptide; 2) to enhance a property of a tumor antigen polypeptide, such as protein stability in an expression system or the stability of protein-protein binding; 3) to provide a novel activity or property to a tumorantigen polypeptide, such as addition of an antigenic epitope or addition of a detectable moiety; or 4) to provide equivalent or better binding to a MHC molecule.

Modifications to a tumor antigen polypeptide are typically made to the nucleic acid which encodes the tumor antigen polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the tumor antigen amino acid sequence. One of skill in the art will be familiar with methods for predicting the effect on protein conformation of a change in protein sequence, and can thus "design" a variant tumor antigen polypeptide according to known methods. One example of such a method is described by Dahiyat and Mayo in *Science* 278:82-87, 1997, whereby proteins can be designed de novo. The method can be applied to a known protein to vary only a portion of the polypeptide sequence. By applying the computational methods of Dahiyat and Mayo, specific variants of a tumor antigen polypeptide can be proposed and tested to determine whether the variant retains a desired conformation.

In general, variants include tumor antigen polypeptides which are modified specifically to alter a feature of the polypeptide unrelated to its desired physiological activity. For example, cysteine residues can be substituted or deleted to prevent unwanted disulfide linkages. Similarly, certain amino acids can be changed to enhance expression of a tumor antigen polypeptide by eliminating proteolysis by proteases in an expression system (e.g., dibasic amino acid residues in yeast expression systems in which KEX2 protease activity is present).

Mutations of a nucleic acid which encode a tumor antigen polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant tumor antigen polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a tumor antigen gene or cDNA clone to enhance expression of the polypeptide. The activity of variants of tumor antigen polypeptides can be tested by cloning the gene encoding the variant tumor antigen polypeptide into a bacterial or mammalian expression vector, introducing the vector into an appropriate host cell, expressing the variant tumor antigen polypeptide, and testing for a functional capability of the tumor antigen polypeptides as disclosed herein. For example, the variant tumor antigen polypeptide can be tested for reaction with autologous or allogeneic sera. Preparation of other variant polypeptides may favor testing of other activities, as will be known to one of ordinary skill in the art.

The skilled artisan will also realize that conservative amino acid substitutions may be made in immunogenic tumor antigen polypeptides to provide functionally equivalent variants, or homologs of the foregoing polypeptides, i.e., the variants retain the functional capabilities of the immunogenic tumor antigen polypeptides. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods, e.g. Molecular Cloning: A Laboratory Manual, J. Sambrook, et al., eds., Second Edition, Cold Spring Harbor Laboratory Press, Cold Spring Harbor, N.Y., 1989, or Current Protocols in Molecular Biology, F. M. Ausubel, et al., eds., John Wiley & Sons, Inc., New York. Exemplary functionally equivalent variants or homologs of the tumor antigen polypeptides include conservative amino acid substitutions of in the amino acid sequences of proteins disclosed herein. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D. Therefore, one can make conservative amino acid substitutions to the amino acid sequence of the tumor antigen disclosed herein and retain the specific antibody-binding characteristics of the antigens.

Likewise, upon determining that a peptide derived from a tumor antigen polypeptide is presented by an MHC molecule and recognized by antibodies or T lymphocytes (e.g., helper T cells or CTLs), one can make conservative amino acid substitutions to the amino acid sequence of the peptide, particularly at residues which are thought not to be direct contact points with the MHC molecule. For example, methods for identifying functional variants of HLA class U binding peptides are provided in a published PCT application of Strominger and Wucherpfennig (PCT/US96/03182). Peptides bearing one or more amino acid substitutions also can be tested for concordance with known HLA/MHC motifs prior to synthesis using, e.g. the computer program described by D'Amaro and Drijfhout (D'Amaro et al., *Human Immunol.* 43:13-18, 1995; Drijfhout et al., *Human Immunol.* 43:1-12, 1995). The substituted peptides can then be tested for binding to the MHC molecule and recognition by antibodies or T lymphocytes when bound to MHC. These variants can be tested for improved stability and are useful, inter alia, in vaccine compositions.

Conservative amino-acid substitutions in the amino acid sequence of tumor antigen polypeptides to produce functionally equivalent variants of tumor antigen polypeptides typically are made by alteration of a nucleic acid encoding a tumor antigen polypeptide. Such substitutions can be made by a variety of methods known to one of ordinary skill in the art. For example, amino acid substitutions may be made by PCR-directed mutation, site-directed mutagenesis according to the method of Kunkel (Kunkel, Proc. Nat. Acad. Sci. U.S.A. 82: 488-492, 1985), or by chemical synthesis of a gene encoding a tumor antigen polypeptide. Where amino acid substitutions are made to a small unique fragment of a tumor antigen polypeptide, such as an antigenic epitope recognized by autologous or allogeneic sera or T lymphocytes, the substitutions can be made by directly synthesizing the peptide. The activity of functionally equivalent variants of tumor antigen polypeptides can be tested by cloning the gene encoding the altered tumor antigen polypeptide into a bacterial or mammalian expression vector, introducing the vector into an appropriate host cell, expressing the altered polypeptide, and testing for a functional capability of the tumor antigen polypeptides as disclosed herein. Peptides that are chemically synthesized can be tested directly for function, e.g., for binding to antisera recognizing associated antigens.

Methods for preparing antigen presenting cells and methods for preparing antigen-specific T cells from peripheral blood mononuclear cells also are provided. Peripheral blood mononuclear cells (PBMCs) are obtained from a subject using methods known to those of skill in the art. The PBMCs are infected with a recombinant avirulent bacteria having a type III secretion system that expresses an antigen. The PBMCs are cultured using media and methods described in the examples and known to those of ordinary skill in the art. The PBMCs expressing the antigen are isolated as antigen presenting cells (APCs). Antigen-specific T cells are prepared by contacting T cells with APCs. Briefly, PBMCs depleted of $CD4^+$ and $CD8^+$ T cells using antibody coated magnetic beads, are either pulsed with a peptide or infected with bacteria and irradiated. The depleted cells are added to $CD4^+$ or $CD8^+$ T cells. Cell isolation techniques are known to those of ordinary skill in the art and include cell sorting (e.g. FACS), immunoprecipitation, centrifugation etc. In a preferred embodiment the PBMCs are $CD4^-CD8^-$ PBMCs.

According to the invention, the terms "treating" and "treatment" include prophylaxis and therapy. When provided prophylactically, a treatment may be administered to a subject in advance of cancer (e.g., to a subject at risk of cancer) or upon the development of early signs of cancer in a subject. A prophylactic treatment serves to prevent, delay, or reduce the rate of onset of cancer or the appearance of symptoms associated with cancer. When provided therapeutically, a treatment may be administered at (or after) the onset of the appearance of symptoms of actual cancer. Therapy includes preventing, slowing, stopping, or reversing cancer or certain symptoms associated with cancer. In some embodiments, a treatment may serve to reduce the severity and duration of cancer or symptoms thereof. In some embodiments, treating a subject may involve halting or slowing the progression of cancer or of one or more symptoms associated with cancer. In some embodiments, treating a subject may involve preventing, delaying, or slowing the onset or progression of long-term symptoms associated with cancer. In some embodiments, treating a subject may involve complete or partial remission.

As used herein, a "subject" is a mammal, preferably a human, non-human primate, cow, horse, pig, sheep, goat, dog, cat or rodent. In all embodiments, human subjects are preferred. A "subject in need" and "subject in need of treatment" as used herein is a subject that is suspected of having cancer or has been diagnosed with cancer. A subject in need is also a subject at risk of having cancer as determined by associated risk factors including but not limited to smoking, family history, genetic predisposition, and external factors (for example environmental factors).

For human cancers, particular examples include, biliary tract cancer; bladder cancer; breast cancer; brain cancer including glioblastomas and medulloblastomas; cervical cancer; choriocarcinoma; colon cancer including colorectal carcinomas; endometrial cancer; esophageal cancer; gastric cancer; head and neck cancer; hematological neoplasms including acute lymphocytic and myelogenous leukemia, multiple myeloma, AIDS-associated leukemias and adult T-cell leukemia lymphoma; intraepithelial neoplasms including Bowen's disease and Paget's disease; liver cancer; lung cancer including small cell lung cancer and non-small cell lung cancer; lymphomas including Hodgkin's disease and lymphocytic lymphomas; neuroblastomas; oral cancer including squamous cell carcinoma; osteosarcomas; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, synovial sarcoma, neurosarcoma, chondrosarcoma, Ewing sarcoma, malignant fibrous histocytoma, glioma, esophageal cancer, hepatoma and osteosarcoma; skin cancer including melanomas, Kaposi's sarcoma, basocellular cancer, and squamous cell cancer; testicular cancer including germinal tumors such as seminoma, non-seminoma (teratomas, choriocarcinomas), stromal tumors, and germ cell tumors; testicular cancer; thyroid cancer including thyroid adenocarcinoma and medullar carcinoma; transitional cancer and renal cancer including adenocarcinoma and Wilms tumor.

The invention also contemplates the use of the methods of the invention in combination with conventional cancer treatment methods and procedures. Conventional treatment for cancer may include, but is not limited to: surgical intervention, chemotherapy, radiotherapy, and adjuvant systemic therapies. In one aspect of the invention, treatment may include administering binding polypeptides such as antibodies that specifically bind to the tumor antigen. These binding polypeptides can be optionally linked to one or more detectable markers, antitumor agents or immunomodulators.

The invention involves the use of various materials disclosed herein to "immunize" subjects or as "vaccines". As used herein, "immunization" or "vaccination" means increasing or activating an immune response against an antigen. It does not require elimination or eradication of a condition but rather contemplates the clinically favorable enhancement of an immune response toward an antigen. Generally accepted animal models, can be used for testing of immunization against cancer.

Methods for immunization, including formulation of a vaccine composition and selection of doses, route of administration and the schedule of administration (e.g. primary and one or more booster doses), are well known in the art. The tests also can be performed in humans, where the end point can be to test for the presence of enhanced levels of circulating CTLs against cells bearing the antigen, to test for levels of circulating antibodies against the antigen, to test for the presence of cells expressing the antigen and so forth. It is further contemplated that immunization may be performed using a kit which includes a DNA vaccine vector encoding an antigen and a recombinant avirulent bacteria having a type III secretion system that expresses the antigen. This combination could be seen as a booster for a vaccine that a patient has already received, plus the recombinant bacteria. Alternatively, for tumor antigens, it can be used essentially as a prime-boost combination product. The kit may contain more than one dose of a vaccine against an antigen.

As part of the immunization compositions, recombinant bacteria expressing via a type III secretion system one or more tumor antigen polypeptides or immunogenic fragments thereof are administered, optionally with one or more adjuvants, to induce an immune response or to increase an immune response. Immunization can also be achieved passively by administering a population of antigen presenting cells (APCs) and/or T cells to a subject. The T cells recognize one or more antigens.

An adjuvant is a substance incorporated into or administered with antigen which potentiates the immune response. Adjuvants may enhance the immunological response by providing a reservoir of antigen (extracellularly or within macrophages), activating macrophages and stimulating specific sets of lymphocytes. Adjuvants of many kinds are well known in the art. Specific examples of adjuvants include monophosphoryl lipid A (MPL, SmithKline Beecham), a congener obtained after purification and acid hydrolysis of *Salmonella minnesota* Re 595 lipopolysaccharide; saponins including QS21 (SmithKline Beecham), a pure QA-21 saponin purified from Quillja *saponaria* extract; DQS21, described in PCT application WO96/33739 (SmithKline Beecham), ISCOM (CSL Ltd., Parkville, Victoria, Australia) derived from the bark of the Quillaia *saponaria* molina tree; QS-7, QS-17, QS-18, and QS-L1 (So et al., Mol. Cells. 7:178-186, 1997); incomplete Freund's adjuvant; complete Freund's adjuvant; montanide; alum; CpG oligonucleotides (see e.g. Kreig et al., Nature 374:546-9, 1995) and other immunostimulatory oligonucleotides; various water-in-oil emulsions prepared from biodegradable oils such as squalene and/or tocopherol; and factors that are taken up by the so-called 'toll-like receptor 7' on certain immune cells that are found in the outside part of the skin, such as imiquimod (3M, St. Paul, Minn.). Preferably, the antigens are administered mixed with a combination of DQS21/MPL. The ratio of DQS21 to MPL typically will be about 1:10 to 10:1, preferably about 1:5 to 5:1 and more preferably about 1:1. Typically for human administration, DQS21 and MPL will be present in a vaccine formulation in the range of about 1 μg to about 100 μg. Other adjuvants are known in the art and can be used in the invention (see, e.g. Goding, Monoclonal Antibodies: Principles and Practice, 2nd Ed., 1986). Methods for the preparation of mixtures or emulsions of polypeptide and adjuvant are well known to those of skill in the art of vaccination.

Other agents which stimulate the immune response of the subject can also be administered to the subject. For example, other cytokines are also useful in vaccination protocols as a result of their lymphocyte regulatory properties. Many other cytokines useful for such purposes will be known to one of ordinary skill in the art, including interleukin-12 (IL-12) which has been shown to enhance the protective effects of vaccines (see, e.g., *Science* 268: 1432-1434, 1995), GM-CSF and IL-18. Thus cytokines can be administered in conjunction with antigens and adjuvants to increase the immune response to the antigens. There are a number of additional immune response potentiating compounds that can be used in vaccination protocols. These include costimulatory molecules provided in either protein or nucleic acid form. Such costimulatory molecules include the B7-1 and B7-2 (CD80 and CD86 respectively) molecules which are expressed on dendritic cells (DC) and interact with the CD28 molecule expressed on the T cell. This interaction provides costimulation (signal 2) to an antigen/MHC/TCR stimulated (signal 1) T cell, increasing T cell proliferation, and effector function. B7 also interacts with CTLA4 (CD152) on T cells and studies involving CTLA4 and B7 ligands indicate that the B7-CTLA4 interaction can enhance antitumor immunity and CTL proliferation (Zheng et al., *Proc. Nat'l Acad. Sci. USA* 95:6284-6289, 1998).

B7 typically is not expressed on tumor cells so they are not efficient antigen presenting cells (APCs) for T cells. Induction of B7 expression would enable the tumor cells to stimulate more efficiently CTL proliferation and effector function. A combination of B7/IL-6/IL-12 costimulation has been shown to induce IFN-gamma and a Th1 cytokine profile in the T cell population leading to further enhanced T cell activity (Gajewski et al., *J. Immunol.* 154:5637-5648, 1995). Tumor cell transfection with B7 has been discussed in relation to in vitro CTL expansion for adoptive transfer immunotherapy by Wang et al. (*J. Immunother.* 19:1-8, 1996). Other delivery mechanisms for the B7 molecule would include nucleic acid (naked DNA) immunization (Kim et al., *Nature Biotechnol.* 15:7:641-646, 1997) and recombinant viruses such as adeno and pox (Wendtner et al., *Gene Ther.* 4:726-735, 1997). These systems are all amenable to the construction and use of expression cassettes for the coexpression of B7 with other molecules of choice such as the antigens or fragment(s) of antigens discussed herein (including polytopes) or cytokines. These delivery systems can be used for induction of the appropriate molecules in vitro and for in vivo vaccination situations. The use of anti-CD28 antibodies to directly stimulate T cells in vitro and in vivo could also be considered. Similarly, the inducible co-stimulatory molecule ICOS which induces T cell responses to foreign antigen could be modulated, for example, by use of anti-ICOS antibodies (Hutloff et al., *Nature* 397:263-266, 1999).

Lymphocyte function associated antigen-3 (LFA-3) is expressed on APCs and some tumor cells and interacts with CD2 expressed on T cells. This interaction induces T cell IL-2 and IFN-gamma production and can thus complement but not substitute, the B7/CD28 costimulatory interaction (Parra et al., *J. Immunol.*, 158:637-642, 1997; Fenton et al., *J. Immunother.*, 21:95-108, 1998).

Lymphocyte function associated antigen-1 (LFA-1) is expressed on leukocytes and interacts with ICAM-1 expressed on APCs and some tumor cells. This interaction induces T cell IL-2 and IFN-gamma production and can thus complement but not substitute, the B7/CD28 costimulatory interaction (Fenton et al., *J Immunother.*, 21(2):95-108, 1998). LFA-1 is thus a further example of a costimulatory molecule that could be provided in a vaccination protocol in the various ways discussed above for B7.

Complete CTL activation and effector function requires Th cell help through the interaction between the Th cell CD40L (CD40 ligand) molecule and the CD40 molecule expressed by DCs (Ridge et al., Nature 393:474, 1998; Bennett et al., Nature 393:478, 1998; Schoenberger et al., Nature 393:480, 1998). This mechanism of this costimulatory signal is likely to involve upregulation of B7 and associated IL-6/IL-12 production by the DC (APC). The CD40-CD40L interaction thus complements the signal 1 (antigen/MHC-TCR) and signal 2 (B7-CD28) interactions.

The use of anti-CD40 antibodies to stimulate DC cells directly, would be expected to enhance a response to tumor associated antigens which are normally encountered outside of an inflammatory context or are presented by non-professional APCs (tumor cells). Other methods for inducing maturation of dendritic cells, e.g., by increasing CD40-CD40L interaction, or by contacting DCs with CpG-containing oligodeoxynucleotides or stimulatory sugar moieties from extracellular matrix, are known in the art. In these situations Th help and B7 costimulation signals are not provided. This mechanism might be used in the context of antigen pulsed DC based therapies or in situations where Th epitopes have not been defined within known tumor associated antigen precursors.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents.

As used herein, the term "pharmaceutically acceptable" means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The therapeutics of the invention can be administered by any conventional route, including injection or by gradual infusion over time. The administration may, for example, be oral (including nasal, vaginal, rectal, mucosal surface), intravenous, intratumoral, intraperitoneal, intramuscular, intracavity, subcutaneous, or transdermal. In preferred embodiments the composition is administered orally or intratumorally.

The preparations of the invention are administered in effective amounts. An effective amount is that amount of a pharmaceutical preparation that alone, or together with further doses, stimulates the desired response. In the case of treating cancer, the desired response is inhibiting the progression of the cancer. This may involve only slowing the progression of the disease temporarily, although more preferably, it involves halting the progression of the disease permanently. In the case of inducing an immune response, the desired response is an increase in antibodies or T lymphocytes which are specific for the tumor antigen(s) employed. These desired responses can be monitored by routine methods.

Where it is desired to stimulate an immune response using a therapeutic composition of the invention, this may involve the stimulation of a humoral antibody response resulting in an increase in antibody titer in serum, a clonal expansion of cytotoxic lymphocytes, or some other desirable immunologic response. It is believed that doses of immunogens ranging from one nanogram/kilogram to 100 milligrams/kilogram, depending upon the mode of administration, would be effective. The preferred range is believed to be between 500 nanograms and 500 micrograms per kilogram. The absolute amount will depend upon a variety of factors, including the material selected for administration, whether the administration is in single or multiple doses, and individual patient parameters including age, physical condition, size, weight, and the stage of the disease. These factors are well known to those of ordinary skill in the art and can be addressed with no more than routine experimentation.

It is further contemplated that administration of the therapeutic composition of the invention, when administered in combination with other factors can occur subsequently, concurrently, or simultaneously. One of ordinary skill in the art would be able to determine the required administration procedure using no more than routine experimentation.

EXAMPLES

Example 1

In Vivo Antigen Delivery by Salmonella Type III Secretion System for Therapeutic Cancer Vaccine Materials and Methods
Mice Female BALB/c mice and C.B-17 scid mice were purchased from CLEA JAPAN (Osaka, Japan) and used at 7-10 weeks of age. Mice were maintained at the Animal Center of Mie University School of Medicine (Mie, Japan). The experimental protocol was approved by the Ethics Review Committee for Animal Experimentation of Mie University School of Medicine.
Patients and Effector T Cells Patients NW29 and NW634 had NY-ESO-1 expressing melanoma and described previously (35, 36). All samples were collected after informed consent as a part of study approved by the Ethics Committee of Landesärztekammer Hessen, Frankfurt. The HLA-A*0201-restricted CD8+ T cell clone specific for NY-ESO-1$_{157-165}$, Clone 49, was generated by limiting dilution from tumor infiltrating lymphocytes of a melanoma patient (kind gift of Dr. D. Valmori, Columbia University, New York, N.Y.) (Valmori, D. et al., Cancer Res. 60:4499-506, 2000). The HLA-A*0201-restricted CD8+ T cell line specific for Influenza matrix$_{58-66}$, NW46-Flu, was derived from NW46 melanoma patient.
Bacterial Strains The S. typhimurium ΔphoP-phoQ strain has been previously described (19). This strain was used to host plasmids expressing a chimeric protein consisting of the first 100 amino acids of SopE, which contains its secretion and translocation signals (38), fused to full length NY-ESO-1 (S. typhimurium-NY-ESO-1), or fused to amino acids 58- to 66 of the influenza virus matrix protein (S. typhimurium-Flu matrix). The S. typhimurium control strain used in these studies is identical to the strains described above except that the plasmid expresses just the first 100 amino acids of SopE. All constructs contain two epitopes placed immediately adjacent to SopE$^{1-100}$: an M45 epitope tag from the adenovirus E4-6/7 protein (39) for chimeric protein detection, and an a mouse H-2$^b$ haplotype Class-I restricted epitope consisting of residues 366 through 374 from the influenza virus nucleoprotein. The control type III secretion-deficient strain used in FIG. 1b and the translocation-deficient strain used in FIG. 1c, have been previously described (40, 41). All plasmids were constructed using standard recombinant DNA methodologies. Analysis of culture supernatant proteins by the different vaccine constructs and translocation of type III secreted proteins into host cells were carried out as previously described (19) using an Ab directed to the M45 epitope tag present in the constructs.

Tumors

Human melanoma cell lines SK-MEL-37, which expresses NY-ESO-1, and SK-MEL-21, which does not express NY-ESO-1, are both HLA-A*0201$^+$. CMS5 is a 3-methylchoranthrene-induced sarcoma cell line of BALB/c origin (DeLeo, A. B., *J. Exp. Med.* 146:720-34, 1977). CMS5a is a subcloned cell line obtained from CMS5, a tumor expressing mERK2 (42, 43). CMS5a-NY-ESO-1 and CMS5a-HE are cell lines derived from CMS5a stably transfected with NY-ESO-1 or c-erbB-2/HER2/neu, respectively (Mukai, K. et al., *Gene Ther.* 9:879-88, 2002). P1.HTR is a subline of mastocytoma P815 of DBA/2 origin (Van Pel, A., et al., *Somat. Cell. Mol. Genet.* 11:467-75, 1985).

Antibodies and Reagents

The hybridomas for anti-CD4 mAb (GK1.5, rat IgG2b) and anti-CD8 mAb (19/178, rat IgG2b) were inoculated to C.B-17 scid mice to collect ascites fluid. Both were used in the form of 25 μl ascites and injected to mice through the lateral tail vein every 5 days for depletion experiments. CD8$^+$ or CD4$^+$ T cells were depleted by the tail-vein administration of anti-CD4 (GK1.5, rat IgG2b) or anti-CD8 (19/178, rat IgG2b) mAb as described previously (46, 47). Synthetic peptides of NY-ESO-1$_{79-108}$ (GARGPESRLLEFYLAMPFATPMEAELARRS, SEQ ID NO:1) and influenza NP$_{206-229}$ (FWRGENGRKTRIAYERMCNILKGK, SEQ ID NO:2) (Gnjatic, S. et al., *Proc. Natl. Acad. Sci. USA.* 100:8862-7, 2003) were obtained from Multiple Peptide Systems (San Diego, Calif.). Recombinant Fowlpox vectors were obtained from Therion Biologics (Cambridge, Mass.) as previously described (Gnjatic, S. et al., *Proc. Natl. Acad. Sci. USA.* 97:10917-22, 2000). A cDNA encoding NY-ESO-1 was cloned into pCAGGS-New (Niwa, H., et al., *Gene.* 108:193-9, 1991) that was kindly provided by Dr. J. Miyazaki (Osaka University, Osaka, Japan) and purified using QIAGEN EndoFree Plasmid Mega Kit (QIAGEN, Hilden, Germany).

Salmonella infection

ΔphoP-phoQ *Salmonella typhimurium* constructs where bacterial type III-secreted protein SopE is fused with full-length NY-ESO-1 (Sal-NY-ESO-1), influenza matrix peptide epitope 58-66 (Sal-Flu matrix), or control vector (Sal-ContVec) were prepared as described previously (Russmann, H. et al., *Science.* 281:565-8, 1998; Shams, H., et al., *Vaccine.* 20: 577-85, 2001; Evans, D. T. et al., *J. Virol.* 77:2400-9, 2003; Galan, J. E., et al., *Gene.* 94:29-35, 1990). *Salmonella typhimurium* infection was performed as previously described with some modifications (Russmann, H. et al., *Science.* 281:565-8, 1998; Shams, H., et al., *Vaccine.* 20: 577-85, 2001; Evans, D. T. et al., *J. Virol.* 77:2400-9, 2003). Briefly, *Salmonella typhimurium* were grown in Lennox broth containing 300 mM NaCl to induce the expression of components of the type III secretion apparatus. To prepare *Salmonella typhimurium* for inoculation of cell cultures or mice, bacteria were cultured overnight at 37° C. and diluted with the appropriate volume of medium to yield an optical density (OD600) of ~0.2. Cultures were further incubated at 37° C. on a rotating wheel to an OD600 of ~0.6. The dose for infection was estimated from a standard curve constructed relating OD value and colony forming units of *Salmonella typhimurium*.

Target cells were infected by co-cultivation at 37° C. for 1 h with each of the *Salmonella typhimurium* at a multiplicity of infection (MOI) of 40. Subsequently, extracellular bacteria were killed by transferring the target cells to RPMI 1640 medium with containing 100 μg/ml gentamicin (Sigma) and incubating at 37° C. for 1 h. Infected cells were subsequently used as APC.

Immunocytochemistry and Immunohistochemistry

Cytospin specimens of ~5×10$^3$ cells were air-dried for 20 min at room temperature and fixed with 10% buffered formalin for 20 min. Specimens were then rinsed three times with PBS and incubated with 1 μg/ml of the anti-NY-ESO-1 mouse mAb, ES121 for 2 hs at room temperature. Dextran polymer labeled system (EnVision Plus, DAKO, Glostrup, Denmark) was used for secondary detection. 3,3'-diamino-benzidine (DAB, BioGenex, San Ramon, Calif.) was used as chromogen and was counterstained with Hematoxylin. For immunohistochemical analyses, surgically removed tumor specimens were sliced into 2 mm thickness, then fixed in 10% paraformaldehyde for 7 hs at 4° C. Fixed specimens were dehydrated and mounted on paraffin. 2.5 μm sliced specimens were used. Immunohistochemistry was performed using the Histomouse-SP Plus Kit (Zymed Laboratories Inc., South San Francisco, Calif.). Antigen retrieval was performed by heating deparaffined specimen at 105° C. for 20 min in DAKO high pH Target Retrieval Solution (Dako, Glostrup, Denmark). Primary Ab ES121 at 2.5 μg/ml concentration was incubated for 16 hs at 4° C. DAB was used as chromogen. Hematoxylin counterstain was performed.

In Vitro Presensitization

In vitro presensitization was performed as previously described (Gnjatic, S. et al., *Proc. Natl. Acad. Sci. USA.* 100:8862-7, 2003; Jager, E. et al., *Proc. Natl. Acad. Sci. USA.* 97:4760-5, 2000; Atanackovic, D. et al., *J. Immunol. Methods.* 278:57-66, 2003). Briefly, CD4$^+$ and CD8$^+$ T cells were separated from peripheral blood mononuclear cells (PBMC) of cancer patients using Ab-coated magnetic beads (Dynabeads; Dynal, Oslo, Norway) and seeded into round-bottom 96-well plates (Corning, N.Y.) at a concentration of 5×10$^5$ cells/well in RPMI 1640 medium with 10% human AB serum (Gemini Bio-Products, Woodland, Calif.), L-glutamine (2 mM), penicillin (100 U/ml), streptomycin (100 μg/ml), and 1% nonessential amino acids. As APC for presensitization, PBMC depleted of CD4$^+$ and CD8$^+$ T cells were pulsed with 10 μM of peptide overnight or infected with different *S. typhimurium* constructs for 1 h followed by 1 h treatment of gentamycine (100 μg/ml) and overnight incubation. Expression of NY-ESO-1 was confirmed in CD4$^-$ CD8$^-$ PBMC following *S. typhimurium*-NY-ESO-1 infection. After irradiation, these cells were added to plates containing CD4$^+$ or CD8$^+$ T cells at a concentration of 1×10$^6$ cells/well. After 20 h, interleukin (IL)-2 (10 U/ml; Roche Molecular Biochemicals, Indianapolis, Ind.) and IL-7 (20 ng/ml; R&D Systems, Minneapolis, Minn.) were added. Subsequently, one-half of medium was replaced by fresh medium containing IL-2 (20 U/ml) and IL-7 (40 ng/ml) twice per week.

Generation and Culture of Target Cells

A fraction of CD4$^+$ T cells remaining from the initial separation (see above) was seeded into 24-well plates (Corning Glass, Corning, N.Y.) at a concentration of 2-4×10$^6$ cells/ well in RPMI 1640 medium with 10% human AB serum (Gemini Bio-Products), L-glutamine (2 mM), penicillin (100 U/ml), streptomycin (100 µg/ml), 1% nonessential amino acids and 10 µg/ml phytohaemagglutinin (PHA HA15; Murex Diagnostics, Dartford, U.K.). Cells were fed and expanded twice per week with medium containing IL-2 (10 U/ml) and IL-7 (20 ng/ml). The activated T cell APCs (T-APC) were harvested and used as target cells after 20-30 days of culture.

Epstein Barr virus-transformed B cells (EBV-B cells) were cultured in RPMI 1640 medium supplemented with 10% fetal bovine serum (Sigma), L-glutamine (2 mM), penicillin (100 U/ml) streptomycin (100 µg/ml), and 1% nonessential amino acids.

In all assays, target cells were washed twice to remove serum and peptides (10 µM), recombinant Fowlpox virus (100 plaque forming units per cell) or *Salmonella* constructs (40 MOI) were added and incubated overnight or 1 h at 37° C. followed by 1 h treatment of gentamycin (100 µg/ml), respectively.

Tetramer Staining

Tetramer staining was performed as previously described (Jager, E. et al., *Proc. Natl. Acad. Sci. USA*. 97:4760-5, 2000). Briefly, presensitized CD8$^+$ T cells in 50 µl of PBS containing 2% fetal bovine serum were stained with phycoerythrin (PE)-labeled NY-ESO-1$_{92-100}$/HLA-Cw*0304 tetramers (prepared at the Ludwig Institute Core Facility by Drs. P. Guillaume and I. Luescher, Lausanne, Switzerland) for 15 min at 37° C. before additional staining of Tricolor-CD8 mAb (Caltag Laboratories, South San Francisco, Calif.) for 15 min at 4° C. After washing, results were analyzed by flow cytometry (FACSCalibur; BD Biosciences, San Diego, Calif.).

Enzyme-Linked Immunospot (ELISPOT) Assay

The number of interferon (IFN)-γ secreting peptide-specific CD4$^+$ and CD8$^+$ T cells was assessed by ELISPOT assays as described previously (Mukai, K. et al., *Gene Ther.* 9:879-88, 2002; Gnjatic, S. et al., *Proc. Natl. Acad. Sci. USA*. 100:8862-7, 2003; Jager, E. et al., *Proc. Natl. Acad. Sci. USA*. 97:4760-5, 2000; Atanackovic, D. et al., *J. Immunol. Methods*. 278: 57-66, 2003; Nishikawa, H. et al., *Proc. Natl. Acad. Sci. USA*. 98: 14571-6, 2001). In human ELISPOT assays, flat-bottomed, 96-well nitrocellulose-coated microliter plates (Millipore, Bedford, Mass.) were coated with IFN-γ mAb (1-D1K; MABTECH, Stockholm) and presensitized T cells and target cells (EBV-B cells pulsed with peptides, or infected with recombinant Fowlpox virus (100 PFU per cell) or the different *S. typhimurium* constructs (40 MOI)) were added to each well and incubated for 24 h. Spots were developed using biotinylated anti-IFN-γ (7-B6-1-biotin; MABTECH), alkaline phosphatase conjugated streptavidin (MABTECH, Sweden) and 5-bromo-4-chloro-3-indolyl phosphate/nitroblue tetrazolium (Sigma) and counted with C. T. L. Immunospot analyzer and software (Cellular Technologies, Cleveland, Ohio).

In mice ELISPOT assays, CD8$^+$ T cells were prepared from spleen cells by positive selection on a MACS column. Target cells were P1.HTR transfected (ECM830, BTX Harvard apparatus, Holliston, Mass.) with mRNA transcribed from plasmid DNA of NY-ESO-1, mERK2, c-erbB-2/HER2/neu or EGFP using mMessage mMachine T7 Ultra Capped Transcription Kit (Ambion, Austin, Tex.). 1×10$^5$ CD8$^+$ T cells were cultured for 24 h with 1×10$^5$ MMC-treated P1.HTR transfected with each mRNA in wells of 96-well nitrocellulose-coated microtiter plates (Millipore) coated with rat anti-IFN-γ (R4-6A2, BD PharMingen). Spots were developed using biotinylated anti-IFN-γ (XMG1.2, BD PharMingen), alkaline phosphatase conjugated streptavidin (MABTECH, Sweden), and alkaline phosphatase substrate kit (BioRad, Hercules, Calif.), and subsequently counted.

Immunization By Gene Gun

Gold particles coated with plasmid DNA (1 µg/injection) were prepared and delivered into shaved skin of the abdominal wall of BALB/c mice by a Helios Gene Gun System (BioRad) at a helium discharge pressure of 350-400 psi, as described previously (Nishikawa, H. et al., *Proc. Natl. Acad. Sci. USA*. 98:14571-6, 2001; Nishikawa, H. et al., *Proc. Natl. Acad. Sci. USA*. 100:10902-6, 2003).

Results

Heterologous Secretion and Translocation into Host Cells of NY-ESO-1 Tumor Antigen by the *S. typhimurium* Type III Secretion System The *S. typhimurium* type III secretion system encoded within the pathogenicity island 1 (SPI-1) has been previously utilized for the delivery of heterologous antigens (19). We constructed a *S. typhimurium* ΔphoP ΔphoQ avirulent strain expressing from a plasmid a chimeric protein composed of the first 104 amino acids of the type III secreted protein SopE fused to reporter epitopes (see Materials and Methods) and the entire amino acid sequence of the NY-ESO-1 tumor antigen (*S. typhimurium*-NY-ESO-1). As a control, we utilized the same *S. typhimurium* ΔphoP ΔphoQ avirulent strain carrying and equivalent plasmid that express only the first 104 amino acids of the type III secreted protein SopE and reporter epitopes (see FIG. 1a for a diagram of these plasmid constructs). The SopE-NY-ESO-1 chimeric protein was efficiently secreted into culture supernatants of the *S. typhimurium* vaccine strain but not into supernatants of an isogenic mutant strain defective in the pathogenicity island 1 (SPI-1)-encoded type III secretion system (FIG. 1b). Furthermore, the SopE-NY-ESO-1 protein was delivered into the cytosol of the CMS5a mouse tumor cell line with an efficiency equivalent to that observed for other type III secreted proteins such as SopE itself (FIG. 1c) (22). We then tested whether *S. typhimurium*-NY-ESO-1 could deliver the NY-ESO-1 chimeric protein to the cytosol of infected human melanoma cell line, SK-MEL-21. As shown in FIG. 1d, SK-MEL-21 infected with *S. typhimurium*-NY-ESO-1 but not those infected with the *S. typhimurium* control strain (an identical strain carrying the control plasmid vector) showed significant specific staining when examined by immunocytochemistry using a NY-ESO-1 mAb. Similar transfer of protein was observed after *S. typhimurium*-NY-ESO-1 infection of other cell types, including an epithelial cancer cell line (SK-LC-14) (data not shown). These results indicate that *S. typhimurium*-NY-ESO-1 can efficiently deliver NY-ESO-1 through the *S. typhimurium* type III secretion system.

Figure 2A:
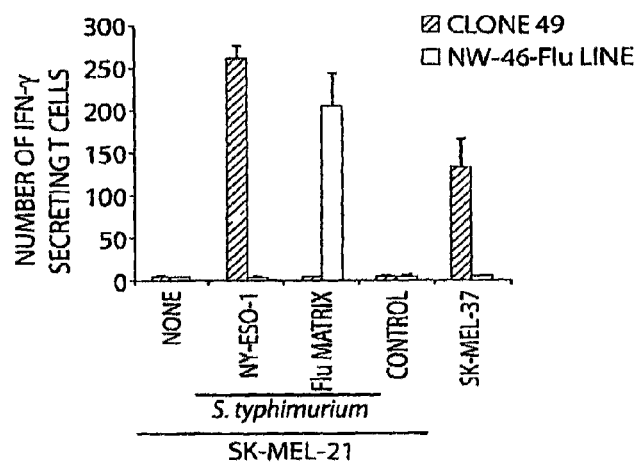
FIG. 2a: HLA-A*0201-restricted CD8$^+$ T cell clone specific for NY-ESO-1$_{157-165}$, clone 49, or HLA-A*0201-restricted CD8$^+$ T cell line specific for Influenza matrix$_{58-66}$, NW46-Flu, were cultured with SK-MEL-21 cells infected with S. typhimurium-NY-ESO-1, S. typhimurium-Flu matrix or S. typhimurium control stain and specific IFN-γ secretion was assessed by ELISPOT assay.

*S. typhimurium* Type III Secretion System Delivers NY-ESO-1 to the MHC Class I and Class II Antigen Presenting Pathway We examined whether NY-ESO-1 delivered by the *S. typhimurium* type III secretion system entered the MHC class I pathway and was presented to CD8$^+$ T cells. SK-MEL-21 cells were infected with *S. typhimurium*-NY-ESO-1, a *S. typhimurium* endowed with the capacity to deliver a peptide derived from the influenza virus matrix protein (*S. typhimurium*-Flu matrix), or the *S. typhimurium* control strain (an identical strain carrying the control plasmid vector). The ability of the infected cells to present antigen to antigen-specific CD8$^+$ T-cells was then evaluated by enzyme-linked immunospot (ELISPOT) assay. The HLA-A*0201-restricted NY-ESO-1$_{157-165}$-specific CD8$^+$ T cell clone, clone 49, was stimulated by *S. typhimurium*-NY-ESO-1-infected SK-MEL-21 cells (FIG. 2a). In contrast, this T cell clone was not stimulated by SK-MEL-21 cells infected with a *S. typhimu*- rium-Flu matrix, even though these infected cells were able to stimulate NW46-Flu, an HLA-A*0201-restricted CD8+ T cell line specific for Influenza matrix$_{58}$-66 (FIG. 2a).

Figure 2B:
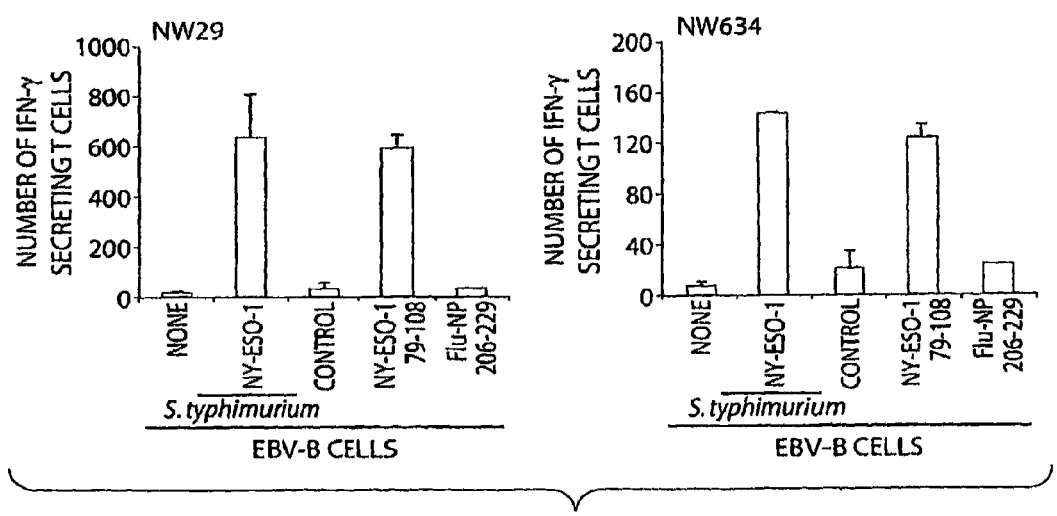
FIG. 2b: CM8$^+$ T cells derived from PBMC of NY-ESO-1 expressing melanoma patients NW29 and NW634 were pre-sensitized by CD4$^-$ CD8$^-$ PBMC pulsed with NY-ESO-1$_{79-108}$ peptide. The induction of CD8$^+$ T cells was analyzed by ELISPOT assay for recognition of autologous EBV-B cells pulsed with peptides or infected with S. typhimurium. These experiments were performed independently three times with similar results. Data are expressed as mean±SD.

We also examined the antigen delivery capacity of the *S. typhimurium* type III secretion system using primary T cells from cancer patients. CD8+ T cells were purified from PBMC of NY-ESO-1-expressing melanoma patients (NW29 and NW634) who had preexisting immunity against NY-ESO-1. Cells were pre-sensitized by autologous CD4⁻ CD8⁻ PBMC pulsed with NY-ESO-1$_{79-108}$ peptide as described in Methods, and antigen-specific IFN-γ secretion of stimulated CD8+ T cells was analyzed by ELISPOT assay. The pre-sensitized primary CD8+ T cells efficiently responded to *S. typhimurium*-NY-ESO-1-infected autologous EBV-transformed B cells (EBV-B cells) in a manner similar to cells pulsed with cognate peptide (FIG. 2b). In contrast, autologous EBV-B cells infected with the *S. typhimurium* control strain or pulsed with a non-cognate peptide did not show any measurable response.

We next asked whether the *S. typhimurium* type III secretion system was able to induce antigen-specific CD8+ T cells from PBMC of cancer patients. CD8+ T cells derived from PBMC obtained from patients NW29 and NW634 were pre-sensitized by CD4⁻ CD8⁻ PBMC infected with *S. typhimurium*-NY-ESO-1 or the control strain, and antigen-specific IFN-γ secretion of CD8+ T cells was analyzed by ELISPOT assay or tetramer staining. Pre-sensitization with CD4⁻ CD8⁻ PBMC infected with *S. typhimurium*-NY-ESO-1, but not with the control strain, induced NY-ESO-1-specific CD8+ T cells (FIGS. 3a and 3b).

Figure 7A:
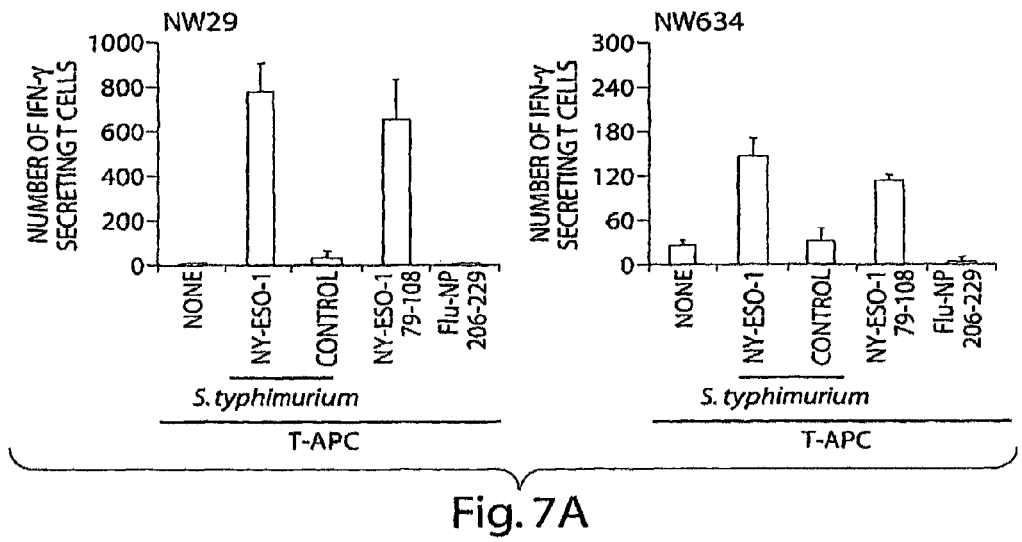
FIG. 7. Antigens delivered by *S. typhimurium* type III secretion are presented to CD4+ T cells CD4+ T cells derived from NW29 and NW634 were presensitized by CD4− CD8− PBMC pulsed with NY-ESO-$1_{79-108}$ peptide (FIG. 7a) or infected with *S. typhimurium*-NY-ESO-1 or *S. typhimurium* control strain (FIG. 7b). The number of specific CD4+ T cells was analyzed by ELISPOT assay for recognition of autologous activated T cell APC pulsed with peptides or infected with recombinant *S. typhimurium* or Fowlpox virus. These experiments were performed independently at least twice with similar results. Data are expressed as mean±SD.
Figure 7B:
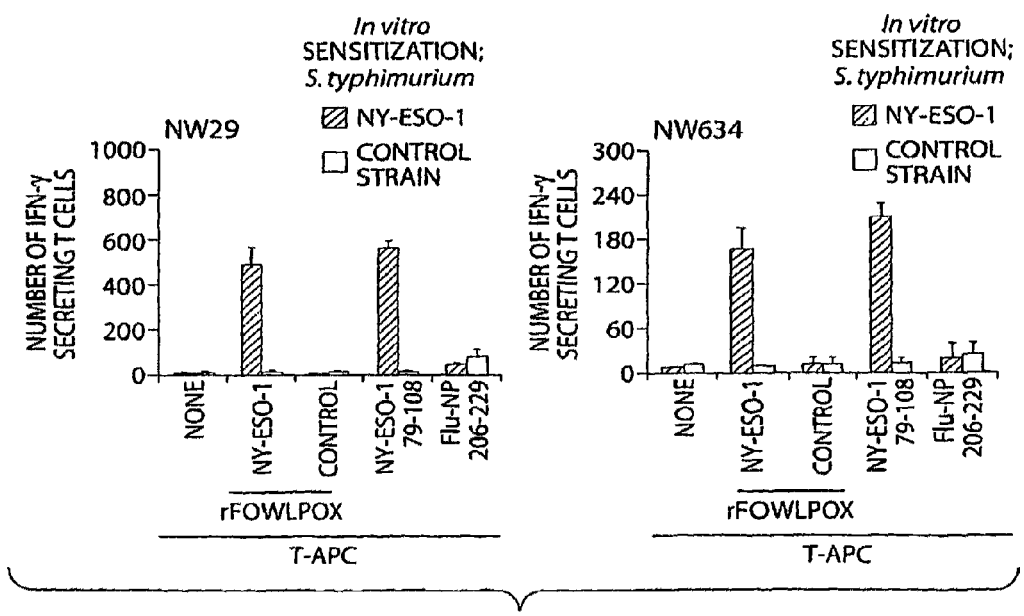

We also examined whether antigens delivered by the *S. typhimurium* type III secretion system could be presented to antigen-specific CD4+ T cells of cancer patients. NY-ESO-1$_{79-108}$ peptide-specific CD4+ T cells responded equivalently to autologous activated T cell APC pulsed with cognate peptide or infected with *S. typhimurium*-NY-ESO-1 (FIG. 7a). Equivalent number of NY-ESO-1$_{79-108}$ peptide-specific CD4+ cells were obtained when CD4+ T cells from NW29 and NW634 were pre-sensitized by CD4⁻ CD8⁻ PBMC infected with *S. typhimurium*-NY-ESO-1 or pulsed with NY-ESO-1 peptide (FIG. 7). Taken together, these results indicate that antigens delivered by the *S. typhimurium* type III secretion system can be efficiently presented to CD8+ and CD4+ T cells.

Figure 4A:
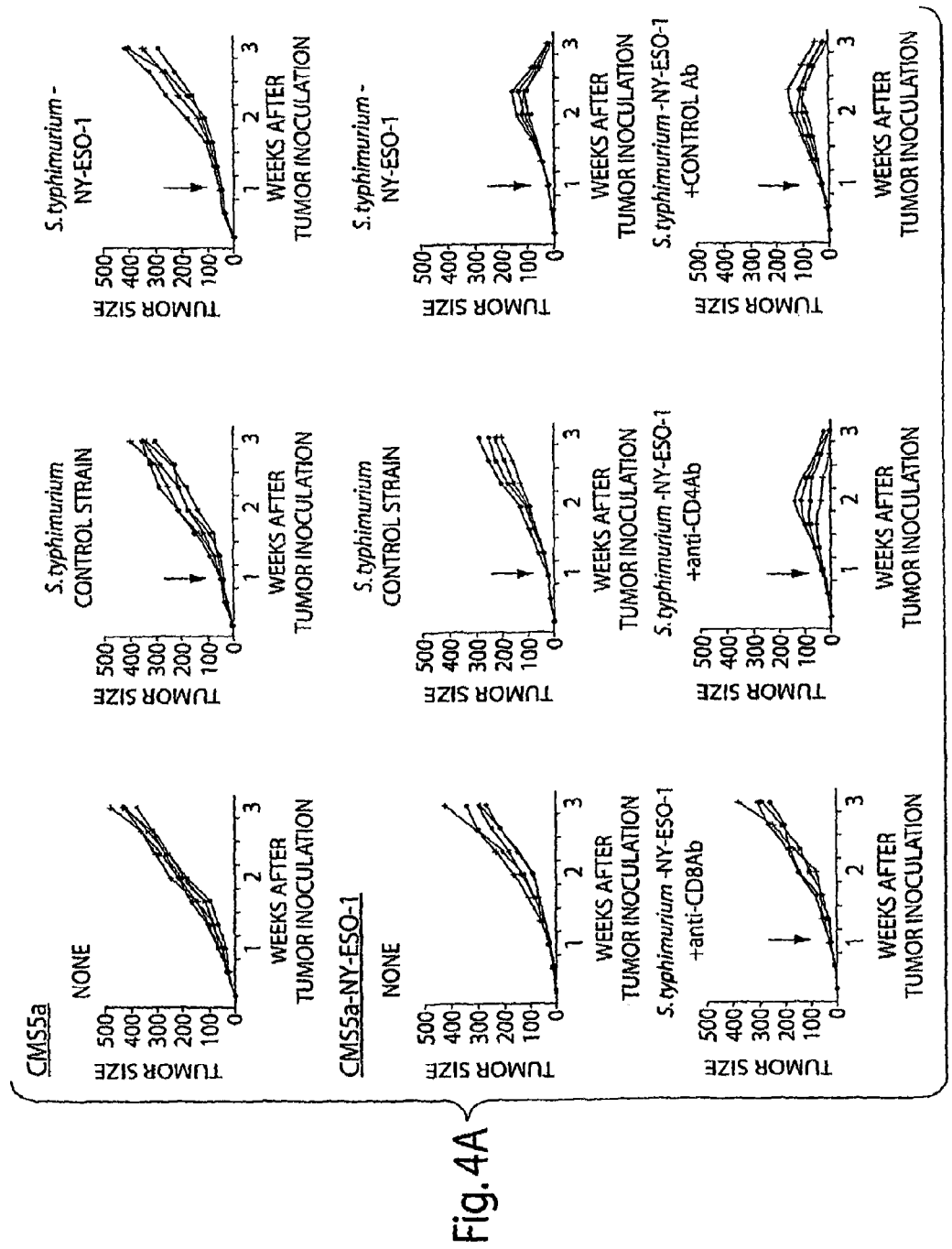
FIG. 4a: BALB/c mice were inoculated with 2×10$^6$ CMS5a-NY-ESO-1 or 1×10$^6$ parental CMS5a and tumor growth was analyzed three times a week. Inoculation with 1-2×10$^8$ S. typhimurium by gavage needle was performed 7 days later. Some groups of mice were also injected intravenously with anti-CD4 or anti-CD8 mAb, or control Ab in the form of 25 μl ascites every 5 days. Arrows represent time points of S. typhimurium oral administration. Each line represents the tumor growth of an individual mouse. Tumor size was evaluated by the formula of longitudinal diameter×horizontal diameter.

Oral Administration of *S. typhimurium*-NY-ESO-1 Causes the Regression of NY-ESO-1 Expressing Tumors in Mice We investigated the potential of *S. typhimurium*-NY-ESO-1 as a therapeutic cancer vaccine by examining its ability to cause the regression of NY-ESO-1-expressing tumors in a mouse model. BALB/c mice were inoculated with 2×10⁶ CMS5a-NY-ESO-1 cells or 1×10⁶ CMS5a parental cells. Seven days after tumor inoculation, animals received an oral administration of 1-2×10⁸ *S. typhimurium*-NY-ESO-1 or the control strain. To monitor the progression of tumor growth, the size of the tumors was measured three times a week. Administration of *S. typhimurium*-NY-ESO-1 or the control strain did not affect the growth of CMS5a tumors when compared with non-treated controls (FIG. 4a). In contrast, administration of *S. typhimurium*-NY-ESO-1 resulted in the regression of CMS5a-NY-ESO-1 tumors (FIG. 4a). The effect was dependent on the delivery of the NY-ESO-1 antigen because mice that received *S. typhimurium* control strain did not show any measurable tumor regression (FIG. 4a).

Figure 4B:
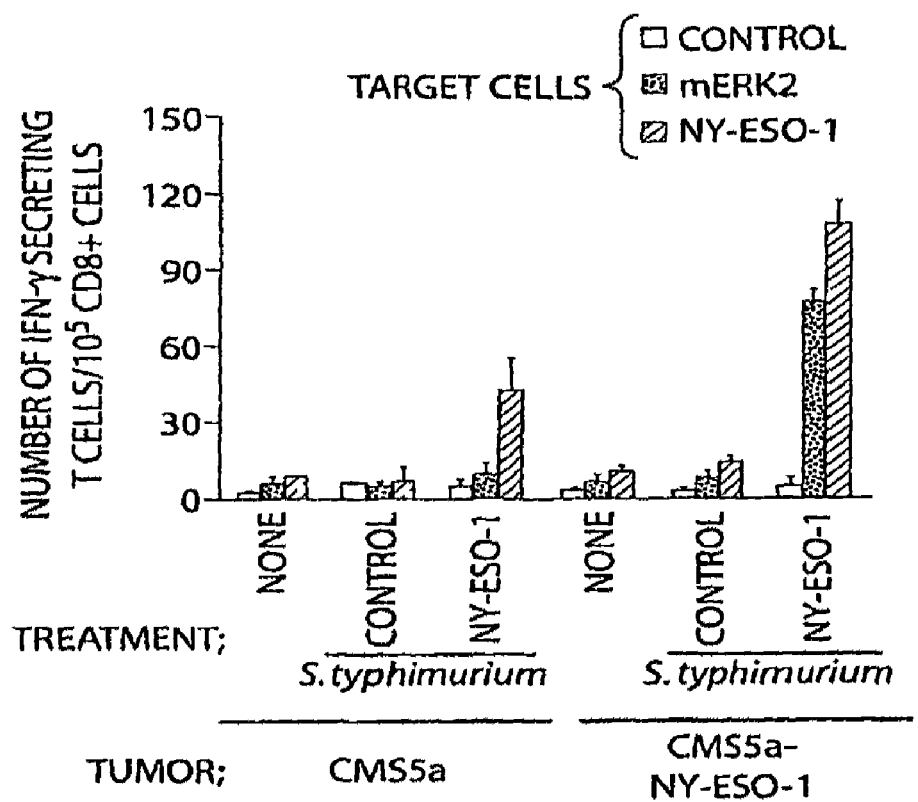
FIG. 4b: CD8$^+$ T cells were purified from spleens of mice bearing CMS5a-NY-ESO-1 without or with administration of S. typhimurium-NY-ESO-1 or the control strain and analyzed for the number of specific IFN-γ producing cells by ELISPOT assay. Data are expressed as mean±SD. These experiments were performed independently at least twice with similar results.

To gain insight into the mechanisms by which *S. typhimurium*-NY-ESO-1 induced tumor regression, we investigated the effect on tumor growth of the depletion of CD8+ or CD4+ T cells from animals that were inoculated with this strain. Injection of anti-CD8 mAb effectively blocked the therapeutic effect of *S. typhimurium*-NY-ESO-1 (FIG. 4a). In contrast, injection of anti-CD4 mAb or an irrelevant control Ab did not affect the ability of *S. typhimurium*-NY-ESO-1 to induce tumor regression. Consistent with the involvement of CD8+ T cells in the therapeutic effect of *S. typhimurium*-NY-ESO-1, mice that were inoculated with this strain developed significant NY-ESO-1-specific CD8+ T cells. In contrast, mice that received the *S. typhimurium* control strain did not have any detectable levels of NY-ESO-1-specific CD8+ T cells (FIG. 4b).

It has been previously shown that certain immunization strategies result in the development of immune response against tumor antigens that are not contained in the vaccine but in tumor cells, a phenomenon known as epitope spreading (23, 24). Therefore, we investigated whether administration of *S. typhimurium*-NY-ESO-1 resulted in the generation of an immune response against antigens not contained in the vaccine but in tumor cells. Mice harboring the CMS5a-NY-ESO-1 tumors that received *S. typhimurium*-NY-ESO-1 developed antigen-specific CD8+ T cells against mutated ERK2 (mERK2), an antigen present in CMS5a tumor cells (FIG. 4b). In contrast, mice harboring CMS5a-NY-ESO-1 inoculated with *S. typhimurium* control strain or mice with CMS5a parental tumors inoculated with *S. typhimurium*-NY-ESO-1 or *S. typhimurium* control strain did not develop any response against mERK2 (FIG. 4b). These results indicate that administration of *S. typhimurium*-NY-ESO-1 can induce immune responses against antigens expressed by the target tumor cells but that are absent from the vaccine, and that these immune responses result in tumor regression.

*S. typhimurium* Delivers Antigen to Target Cells when Administered Intratumorally The efficient in vitro antigen delivery by *S. typhimurium*-NY-ESO-1 prompted us to examine the ability of this vaccine strain to deliver antigen into tumor cells in vivo. *S. typhimurium*-NY-ESO-1 or *S. typhimurium* control strain were directly inoculated into palpable CMS5a tumors (that do not express NY-ESO-1). Inoculated tumors were then removed surgically and analyzed by immunohistochemistry for the presence of NY-ESO-1. NY-ESO-1 was detected in tumor cells inoculated with *S. typhimurium*-NY-ESO-1, but not in tumor cells inoculated with the *S. typhimurium* control strain. NY-ESO-1 was largely detected in areas surrounding necrotic foci (FIG. 5). However, non-specific staining was also observed in necrotic foci resulting from the inoculation (FIG. 5). Although NY-ESO-1 was mainly detected in tumor cells, surrounding stroma containing fibroblasts was also positive for NY-ESO-1 (FIG. 5). These results indicate that the *S. typhimurium* through its type III secretion system can delivered antigen to the tumor site when locally administrated.

Figure 6A:
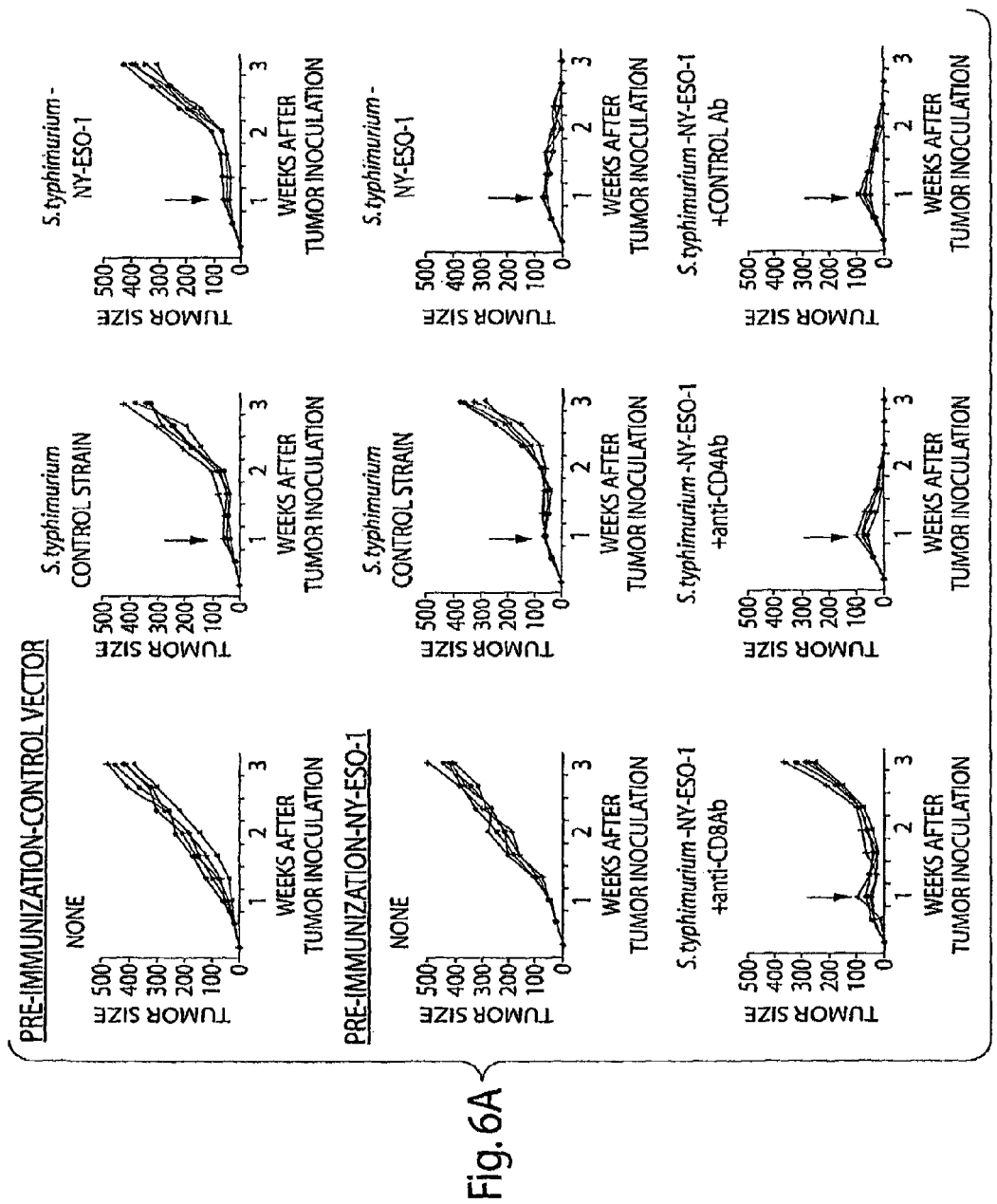
FIG. 6a: BALB/c mice were immunized twice at two-week intervals with plasmid encoding NY-ESO-1 or Control Vector by gene gun. These mice were inoculated with to 2×10$^6$ CMS5a-HE tumor cells (NY-ESO-1 negative) and tumor growth was analyzed three times a week. Seven days later, the injection of 0.5-1×10$^6$ S. typhimurium-NY-ESO-1 or the control strain at the tumor site was performed. Some groups of mice were also injected intravenously with anti-CD4 or anti-CD8 mAb, or control Ab in the form of 25 μl ascites every 5 days. Arrows show time points of S. typhimurium administration. Each line represents the tumor growth of an individual mouse. Tumor size was evaluated by the formula of longitudinal diameter×horizontal diameter.
Figure 6B:
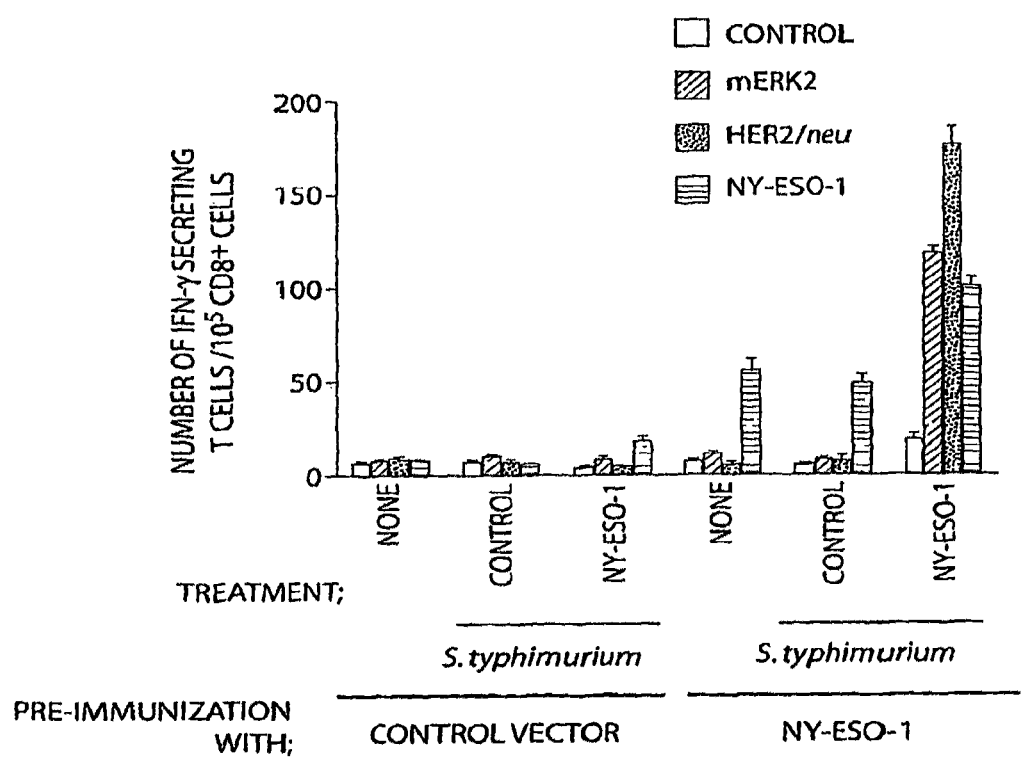
FIG. 6b: CD8+ T cells were purified from spleens from Control vector or NY-ESO-1 pre-immunized mice bearing CMS5a-HE untreated or treated with *S. typhimurium*-NY-ESO-1 or the control strain and analyzed for the number of specific IFN-γ producing cells by ELISPOT assay. Data are expressed as mean±SD. These experiments were performed independently at least twice with similar results.

Local Tumor Antigen Delivery by the *S. typhimurium* Type III Secretion System Leads to Epitope Spreading and Tumor Regression Given the efficient antigen delivery by *S. typhimurium*-NY-ESO-1 into tumor cells in vivo, we asked whether the *S. typhimurium* type III secretion system could be used to transfer NY-ESO-1 into tumor cells that do not express that antigen, and render them susceptible to preexisting NY-ESO-1-specific CD8+ T cells. We therefore immunized BALB/c mice by gene gun with plasmids encoding NY-ESO-1 or with control vector plasmids twice in two-week intervals. This immunization strategy resulted in the induction of NY-ESO-1-specific CD8+ T cells in mice immunized with NY-ESO-1 but not in mice immunized with control plasmids (FIG. 6b). Immunized mice were then inoculated with to 2×10⁶ cells of the CMS5a-HE tumor cell line, which expresses tumor-specific antigens mERK2 and c-erbB-2/HER2/neu but does not express NY-ESO-1. Seven days after tumor inoculation, 0.5-1×10$^6$ S. typhimurium-NY-ESO-1 or S. typhimurium control strain were injected directly into the tumor site, and tumor growth was examined three times a week. Administration of S. typhimurium-NY-ESO-1 not only prevented tumor growth in NY-ESO-1 immunized animals but also caused the regression of the incipient tumors (FIG. 6a). In contrast, administration of the S. typhimurium control strain in NY-ESO-1 pre-immunized mice or administration of S. typhimurium-NY-ESO-1 in control plasmids pre-immunized animals caused a slight initial reduction in the rate of tumor growth but tumors finally went on to develop to reach almost the same size as in untreated control animals (FIG. 6a). Intratumoral administration of S. typhimurium-NY-ESO-1 into NY-ESO-1 pre-immunized mice resulted in a significant increase in the levels of NY-ESO-1-specific CD8$^+$ T cells (FIG. 6b). More importantly, these animals also developed CD8$^+$ T cells response against mFRK2 and c-erbB-2/HER2/neu antigens, which are expressed by the tumor cells, but not present in the immunization constructs (FIG. 6b). These effects were not observed in animals that received the S. typhimurium control strain or that had been pre-immunized with control plamids (FIG. 6b). Again, epitope spreading was accompanied with tumor regression. Taken together, these results indicate that delivery of a heterologous antigen into tumor cells by the S. typhimurium type III secretion system renders these cells targets for preexisting CD8$^+$ T cells directed to the heterologous antigen, resulting in epitope spreading and tumor eradication.

Discussion

We have engineered a recombinant S. typhimurium strain that uses a type III protein secretion system to inject into host cells the NY-ESO-1 protein that is produced in the bacteria. We examined the capacity of this strain to elicit in vitro NY-ESO-1-specific CD8$^+$ and CD4$^+$ T cell response in human, to eradicate NY-ESO-1 expressing tumors in mice, and to deliver the antigen to tumor cells in vivo. We showed that S. typhimurium-NY-ESO-1 effectively delivered NY-ESO-1 to human melanoma cells in vitro through its type III secretion system, and these cells were able to present this antigen to T cell clones and lines via the MHC class I pathway (FIGS. 1 and 2a). Antigen presentation by S. typhimurium-NY-ESO-1 infected cells was more efficient than presentation by tumor cells naturally expressing NY-ESO-1 (FIG. 2a), even though the number of NY-ESO-1 expressing cells was lower in S. typhimurium-NY-ESO-1 infected tumor cells compared to tumor cells naturally expressing NY-ESO-1. This suggests a very effective processing of antigens when delivered by the type III secretion system. T cell recognition of S. typhimurium-infected target cells was equivalent to that of peptide pulsed cells (FIG. 2b). S. typhimurium-NY-ESO-1-infected CD4$^-$ CD8$^-$ PBMC from patients who had NY-ESO-1 expressing tumors and preexisting NY-ESO-1 immunity efficiently elicited NY-ESO-1-specific CD8$^+$ and CD4$^+$ T cells. The capacity of S. typhimurium-NY-ESO-1 to elicit NY-ESO-1-specific CD8$^+$ and CD4$^+$ T cells was equivalent to that of recombinant Fowlpox virus or Adenovirus vectors (FIG. 3, Supplemental FIG. 1 and data not shown). Peptide pulsed APC elicited a higher number of tetramer-positive CD8$^+$ T cells compared to S. typhimurium-NY-ESO-1 infected APC, while the number of IFN-γ secreting cells did not differ (FIGS. 2b and 3). This suggests that S. typhimurium may activate effector cells more efficiently than peptides, which lack costimulatory signals and consequently may activate IFN-γ non-secreting CD8$^+$ cells as reported previously (25). We did not observe any inhibition of T cell proliferation with Salmonella in our experimental conditions, though it was recently reported that direct contact-dependent inhibition occurred in longer-term cultures (26). Taken together, the S. typhimurium type III secretion system is an effective NY-ESO-1 antigen delivery platform in humans.

Our data also indicate that the S. typhimurium type III secretion system is also an effective antigen delivery system in vivo. Oral administration of S. typhimurium-NY-ESO-1 into mice harboring NY-ESO-1 expressing tumors resulted in the development of antigen-specific CD8$^+$ T cells and the complete regression of the tumors. The vaccine strain used in these studies is very inefficient at reaching deeper tissues (27) suggesting that the immune response may well be largely primed at mucosal sites. Indeed previous experiments with an equivalent strain carried out in monkeys strongly suggest this possibility (21). However, since low bacterial numbers can reach deeper tissues systemic priming cannot be ruled out. Tumor regression was dependent on the induction of NY-ESO-1-specific CD8$^+$ T-cells since: 1) tumor regression was only observed in animals bearing NY-ESO-1 expressing tumors that received S. typhimurium-NY-ESO-1 but not the S. typhimurium control strain; and 2) depletion of CD8$^+$ cells from immunized animals abrogated tumor regression (FIG. 4). Consequently, the anti-tumor activity of S. typhimurium-NY-ESO-1 is different from a previously reported anti-tumor activity of some avirulent strains of S. typhimurium that, when administered into mice, caused tumor regression. The previously described anti-tumor activity has been ascribed to a direct toxic activity of S. typhimurium on tumor cells, which required the localization of the bacteria within the tumor tissue (28, 29). Under our experimental conditions, the orally administered S. typhimurium ΔphoP ΔphoQ strain utilized in our experiments does not reach tumor local compartments in significant numbers. More importantly, the anti-tumor effect was not observed after administration of an identical control strain carrying the control plasmid vector without the gene encoding SopE-NY-ESO-1 chimeric protein (FIG. 4).

The rapid and effective anti-tumor activity of the S. typhimurium endowed with the ability to deliver a tumor antigen via its type III secretion is striking. It has been previously shown that stimulation of the innate immune system is essential to break immunological tolerance (14). TLR signals, which recognize microbial-associated molecular patterns existing in bacteria such as the S. typhimurium strain utilized in our study, are not only able to block the suppressive activity of CD4$^+$ CD25$^+$ Tregs but also break CD8 tolerance even in the presence of CD4$^+$ CD25$^+$ Tregs (11-13, 15). In our in vivo mouse model, expression of NY-ESO-1 by growing tumor cells alone did not elicit measurable antigen-specific CD8$^+$ T cells. However, upon oral administration of S. typhimurium-NY-ESO-1, animals developed antigen-specific CD8$^+$ T cells and the tumors underwent regression. It is possible that the demonstrated ability of S. typhimurium to strongly stimulate innate immunity may contribute to its ability to induce strong CD8$^+$ response against NY-ESO-1 (16, 17).

Administration of S. typhimurium-NY-ESO-1 at the tumor site of NY-ESO-1 DNA primed animals led to rapid eradication of tumors that did not initially express the NY-ESO-1 antigen. These results were surprising since: 1) tumor eradication was strictly dependent on the delivery of NY-ESO-1 by the S. typhimurium type III secretion system and it was not observed in animals receiving the S. typhimurium control strain; 2) tumor regression was dependent on the presence of CD8$^+$ T cells; and 3) tumor regression was not observed in unprimed animals (FIG. 6). Administration of S. typhimurium at the tumor site caused some necrosis but it was not sufficient in itself to eradicate the tumor (FIGS. 5 and 6a). In this case, we believe that tumor regression was due, at least initially, to the recognition of tumor cells that had received NY-ESO-1 antigen via the *S. typhimurium* type III secretion system by preexisting antigen-specific CD8⁺ T cells. This hypothesis is consistent with the observation that tumor regression was strictly dependent on the presence of preexisting antigen-specific CD8⁺ T cells since mice naïve for NY-ESO-1 failed to prevent the rapid growth of CMS5 tumors. Even though NY-ESO-1 is an immunogenic antigen for mice, intratumoral treatment with *S. typhimurium*-NY-ESO-1 could not elicit specific T cells sufficiently fast to provide protection in the absence of preexisting immunity to NY-ESO-1 (FIG. 6*a*). Since undoubtedly not all tumor cells could have been targeted by *S. typhimurium*-NY-ESO-1, efficient tumor eradication most likely involved the generation of CD8⁺ T cell response against other tumor antigens not present in the vaccine. Consistent with this hypothesis, NY-ESO-1 pre-immunized animals receiving *S. typhimurium*-NY-ESO-1 developed CD8⁺ response against at least two other tumor antigens that were not present in the vaccine presumably by the previously observed phenomenon of "epitope spreading" (23, 24) (FIG. 6*b*). In fact, we believe that "epitope spreading" is also essential for the rapid tumor regression observed after oral administration of *S. typhimurium*-NY-ESO-1 to animals carrying NY-ESO-1-expressing tumors since in this case we also observed the development of CD8⁺ T cells specific to antigens not present in the vaccine (FIG. 6*b*). These data are in line with recent reports that tumor vaccine-induced CTLs act not only as effectors to kill tumor cells bearing the cognate antigen but also generate conditions enabling to stimulate other tumor antigens-specific CTLs (30, 31). *S. typhimurium* has the ability to invade non-phagocytic cells such as epithelial cells (32). As shown in FIG. 5, the *S. typhimurium* type III secretion system injected NY-ESO-1 not only to tumor cells but to surrounding tissues as well. Tumor stromal cells might also be targeted and facilitate tumor eradication (33, 34). One concern to consider is undesired antigen delivery to normal tissue by the *S. typhimurium* vector that could potentially prime autoimmune reactivity. Although after healing, mice treated with intra-tumoral injection of *S. typhimurium* did not exhibit any side effect except local inflammation, further observation might be required to completely rule out this possibility.

Our studies suggest a novel strategy for cancer immunotherapy using the *S. typhimurium* type III secretion system as an antigen delivery platform that would not require prior knowledge of the tumor antigen composition. This strategy would require the administration of a *S. typhimurium* strain engineered to deliver antigen(s) against which the patient would have preexisting CD8⁺ T cells to tumor cells via its type III secretion system. Those antigens would not need to be expressed in tumor antigens. In fact, it is conceivable that preexisting CD8⁺ T cells against viral antigens such as influenza or EB virus, of common occurrence in human populations due to vaccination and/or convalescent immunity, could be used for this purpose.

Example 2

Use of the *Salmonella typhimurium* Type III Secretion System for the Development of Novel Anti-Cancer Vaccines The *S. typhimurium* Type III Secretion Systems (TTSS).
In the last few years, a novel protein secretion pathway has been identified in a variety of pathogenic Gram-negative bacteria, including many potential agents of bioterrorism such as *Yersinia pestis*, *Burkholderia mallei* and *pseudomallei*, and *S. enterica* (Galán, J. E., and A. Colimer, *Science*, 284:1322-1328, 1999). This pathway, which has been named type III or contact dependent, is involved in the secretion and delivery of bacterial effector proteins into the host cell cytosol. These proteins are essential for virulence and have the capacity to modulate cellular functions for the pathogen's benefit. *Salmonella* spp. encode two of these systems that are involved in different stages of the infections process (Galán, J. E., *Annu. Rev. Cell Dev. Biol.*, 17:53-86, 2001). Extensive studies have been conducted to characterize *S. typhimurium* TTSS encoded within the pathogenicity island 1 (SPI-1) of the bacterial chromosome, which is involved in the initial interactions of *Salmonella* with the intestinal epithelium (Galán, J. E., *Curr. Op. Microbiol.*, 2:46-50, 1999). The other system encoded within the pathogenicity island 2 (SPI-2) is essential to establish systemic infection (Hensel, M., *Mol Microbiol.*, 36:1015-23, 2000).

Use of the *S. typhimurium* Type III Secretion System for Antigen Delivery.

Proteins destined to travel through the TTSS pathway posses discrete independent domains that direct their secretion or translocation into the host cell. In general, the first N-terminal 10 to 20 amino acid residues of these proteins are required for their secretion, whereas an adjacent domain of 60 to 80 residues is involved in the binding to specific cognate chaperones and the translocation into the host cell (reviewed in Galán, J. E., and A. Collmer, *Science*, 284:1322-1328, 1999). The secretion and translocation domains of several secreted substrate proteins have defined at the molecular and in some cases even at the atomic levels, including SptP, SopE and InvJ (Russmann, H., et al., *Mol. Microbiol.*, 46:769-7916, 2002; Stebbins, C. E., and J. E. Galán, *Nature*, 414:77-81, 2001). This has allowed development of an antigen delivery system based on the observation that these domains can direct the secretion and translocation of heterologous proteins (U.S. Pat. No. 6,306,387). More importantly, it has been shown that proteins delivered through this system can induce vigorous antibody as well as CD4 and CD8 T cell responses that lead to protection against challenge with a relevant model of infection, utilizing well-defined antigens from the influenza virus and lymphocytic coriomeningitis virus (LCMV) and a mouse model of infection (Russmann, H., et al., *Science*, 281:565-8, 1998; Shams, H., F., et al., *Vaccine*, 20:577-85, 2001). Infection with *Salmonella* recombinants expressing immunodominant CTL epitopes of influenza or lymphocytic coriomeningitis viruses fused to a bacterial protein that can be injected into host cell via the TTSS sensitized cells for CTL recognition in vitro. CTL recognition was MHC class I-restricted and TAP-dependent. Furthermore, immunization of mice with an attenuated strain of *Salmonella* engineered to deliver a single immunodominant CTL epitope of LCMV stimulated potent virus-specific CTL responses that protected against a lethal LCMV challenge. More recently, it was demonstrated that the *Salmonella* type III secretion system efficiently primed antigen-specific mucosal CD8 responses in monkeys. ΔphoP-phoQ-attenuated strains of *S. typhimurium* and *S. typhi* expressing fragments of the SIV Gag protein fused to the type III-secreted SopE protein sensitized rhesus macaque cells for CTL recognition in vitro (Evans, D. T., et al., *J. Virol.*, 77:2400-2409, 2003). Furthermore, Mamu-A*01⁺ macaques inoculated orally with recombinant *Salmonella* developed Gag-specific CTL responses that were significantly boosted upon immunization with modified-vaccinia Ankara expressing SIV Gag (MVA Gag). More importantly, a significant percentage of the Gag-specific T cell population in immunized animals also expressed the intestinal homing receptor α4β7. Additionally, Gag-specific CD8⁺ T cells were detected amongst lymphocytes isolated from the colon indicating that these cells were homing to the gastrointestinal mucosa. These findings demonstrated the potential of mucosal priming by the *Salmonella* TTSS to direct cellular immune responses to the gastrointestinal mucosa of immunized macaques.

Construction of *S. typhimurium* Vaccine Strains for the Delivery of Tumor Antigens.

Figure 1B:
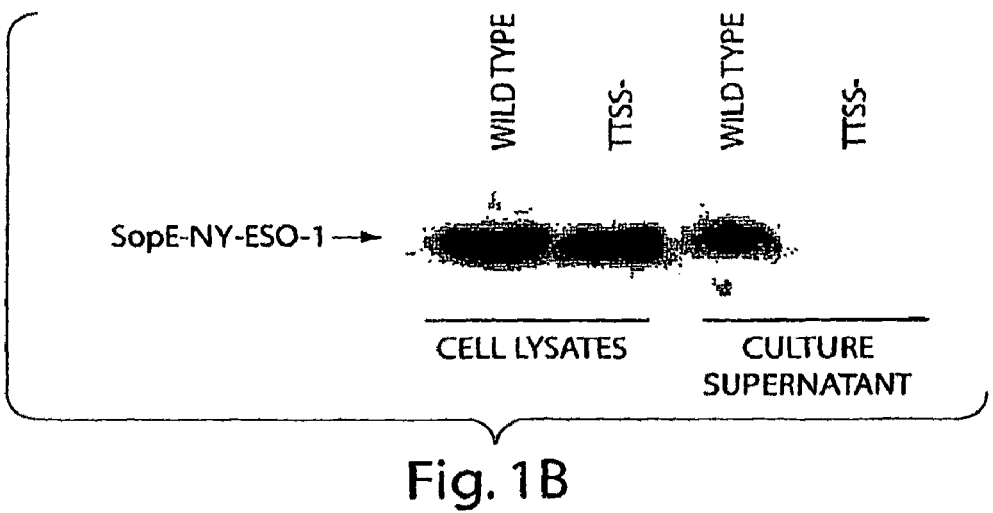
FIG. 1b: A plasmid expressing NY-ESO-1 fused to the type III secretion and translocation signals of SopE (SopE-NY-ESO-1) was introduced into a ΔphoP phoQ S. typhimurium (labeled "wild type") and an isogenic type III secretion-defective invA mutant (labeled "TTSS$^-$"). Whole cell lysates and cultured supernatants of these strains were then examined for the presence of the chimeric SopE-NY-ESO-1 protein by western blotting.
Figure 1C:
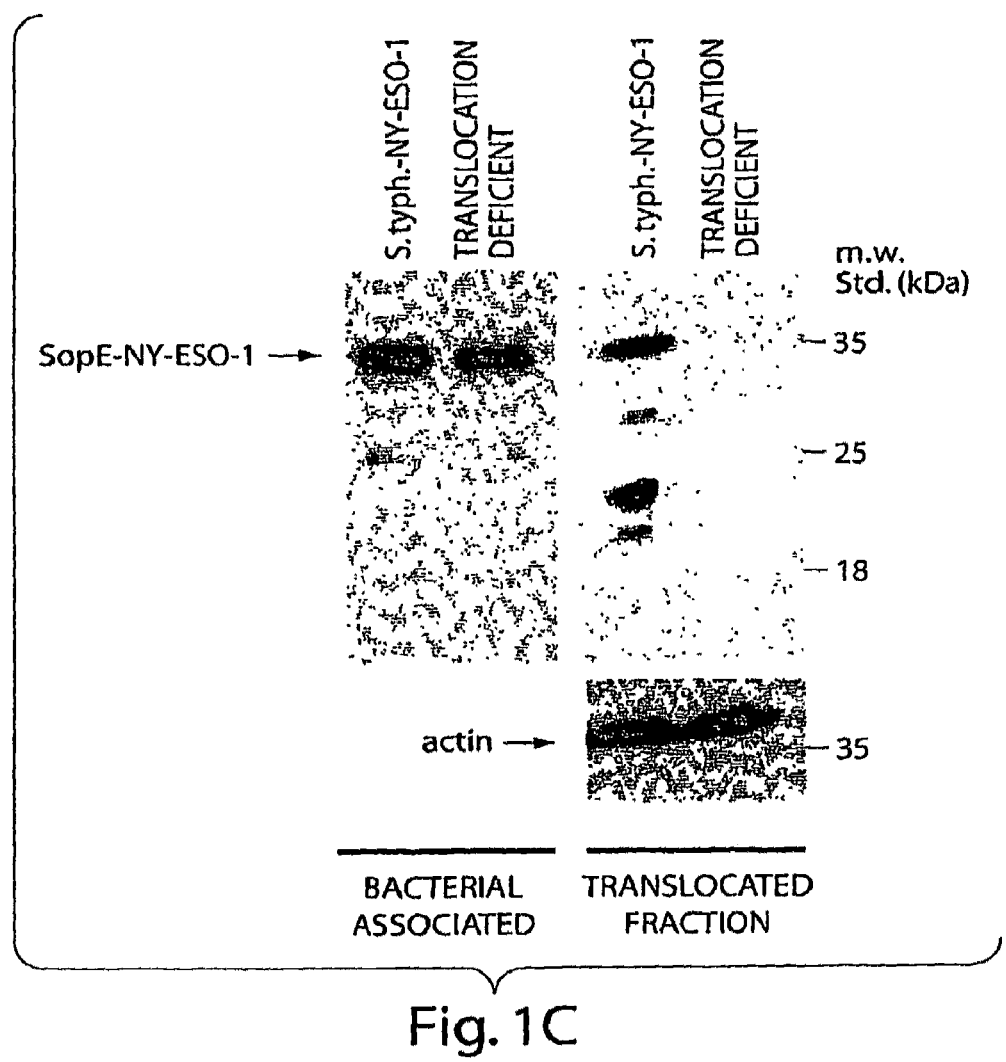
FIG. 1c: Mouse CMS5a tumor cells were infected with S. typhimuriumNY-ESO-1 (indicated "S. typh.-NY-ESO-1") or a translocation-defective strain (indicated "translocation deficient") and the presence of SopE-NY-ESO-1 in the different fractions was examined. Blots containing the translocated protein fraction were re-probed for the host-cell protein to verify equal loading of the samples.
Figure 1D:
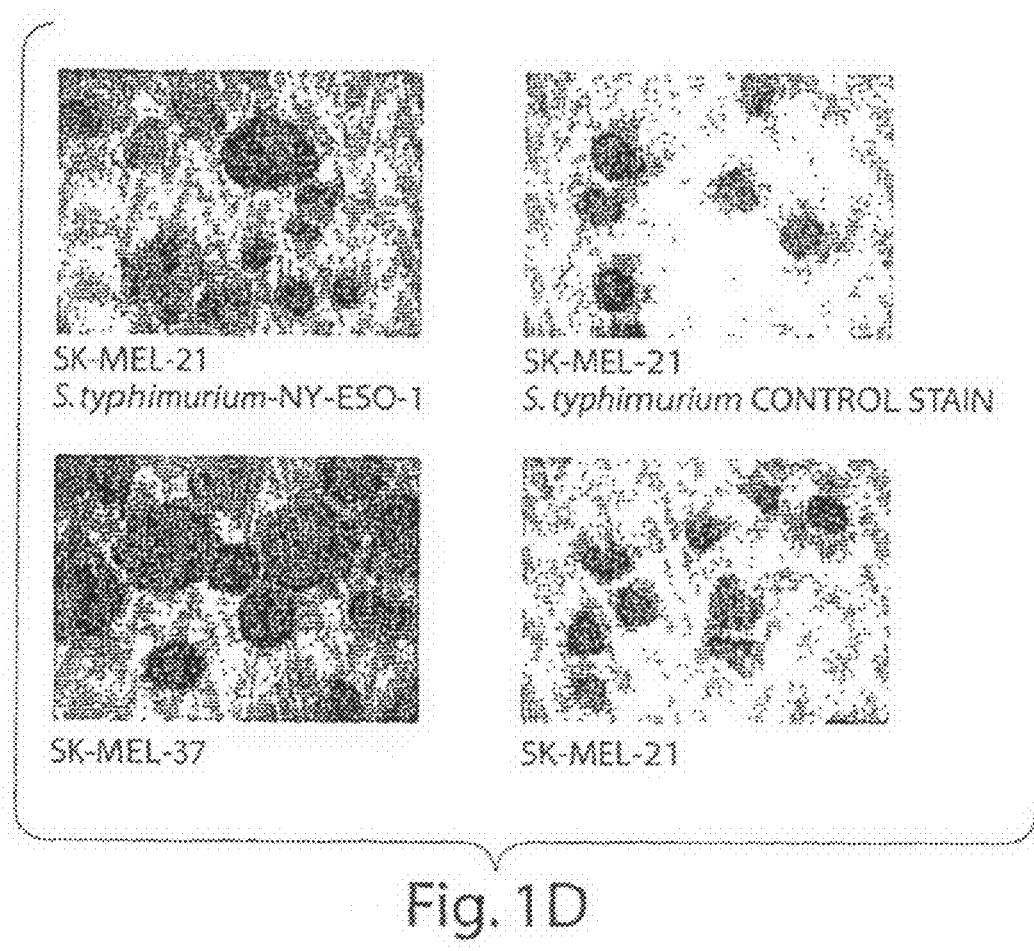
FIG. 1d: SK-MEL-21, a human melanoma cell line that does not express NY-ESO-1, was infected with S. typhimurium-NY-ESO-1 or S. typhimurium control strain and examined by immunocytochemistry with anti-NY-ESO-1 mAb ES121. SK-MEL-37 is served as a positive control of a human melanoma cell line with natural NY-ESO-1 expression.
Figure 8:
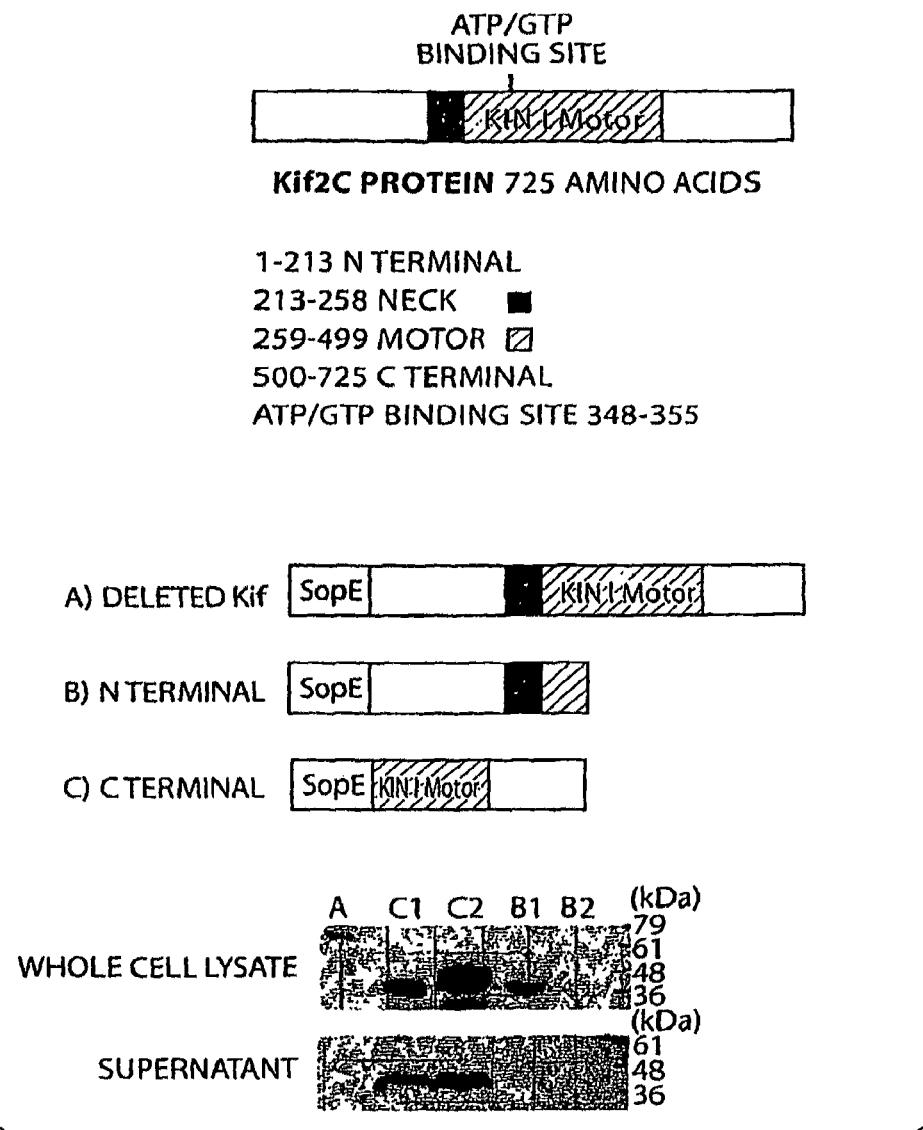
FIG. 8. Expression of NY-CO-58 (kif2c) in *S. typhimurium*.

We have constructed *S. typhimurium* vaccine strains expressing the tumor antigens NY-ESO-1 and NY-CO-58 fused to the secretion and translocation signals of SopE, a *Salmonella* protein delivered into host cells by its type III secretion system (FIG. 1a and FIG. 8). The chimeric proteins were efficiently secreted into culture supernatants and were able to sensitize a variety of cells for recognition by tumor antigen-specific T cell clones. These constructs are tested in human volunteers.

Example 3

Construction of Fusion Proteins for TTSS Delivery

To deliver antigens through the SPI-1 TTSS we have utilized the secretion and translocation signals of SopE (SopE$_{1-104}$) since this domain behaves as an excellent "molecular courier" to deliver heterologous antigens to antigen presenting compartments (Evans, D. T., et al., *J. Virol.*, 77:2400-2409, 2003). cDNAs encoding the tumor antigens NY-ESO-1, have been fused to the secretion and translocation signals of TTSS-secreted proteins such as SopE or SptP both separately and in tandem in a single construct. Construction of the relevant plasmids has been carried out by standard recombinant DNA techniques. The vectors used are those previously described (Evans, D. T., et al., *J. Virol.,* 77:2400-2409, 2003; Russmann, H., et al., *Science,* 281:565-8, 1998). The resulting plasmids were introduced into the *S. typhimurium* ΔphoP phoQ ΔaroA Δasd vaccine strain (Galan, J. E., et al., *Micro. Path.,* 6:433-443, 1989; Galán, J. E., et al., *Gene,* 94:29-35, 1990; Hoiseth, S. K., and B. A. Stocker, *Nature,* 291:238-239, 1981), and as controls for TTSS-dependent secretion, into an invA mutant strain that is defective for the SPI-1 TTSSs (Galán, J. E., et al., *J. Bacteriol.,* 17:4338-4349, 1992). The presence of two attenuating mutations ensures the safety of the constructs while maintaining proficiency for antigen delivery since expression of the SPI-1 TTSS is up-regulated in this particular strain. The backbone of the expression vector is from the low-copy plasmid vector pWSK29 and the genes are expressed from their native promoters (Evans, D. T., et al., *J. Virol.,* 77:2400-2409, 2003; Russmann, H., et al., *Science,* 281:565-8, 1998). In addition, the vector carries the *Salmonella* asd gene to avoid the need for antibiotics to ensure its maintenance (Galán, J. E., et al., *Gene,* 94:29-35, 1990). We have found that this vector backbone/promoter combination provides efficient and stable delivery of antigens in vitro and in vivo. To comply with FDA regulations, no antibiotic genes are present in either the *Salmonella* vaccine strains or the plasmids. In addition, maintenance of the plasmid is ensured with the asd balance/lethal system (Galán, J. E., et al., *Gene,* 94:29-35, 1990). Similar constructs using tumor antigens MAGE-A3, SSX2, SCP1 and CT7 are prepared and tested as described herein.

Evaluation of the Different Constructs for Their Ability to Express and Deliver Tumor Antigens In Vitro.

The fusion proteins have been tested for their ability to be secreted and translocated into cultured host cells by the *S. typhimurium* type III secretion system as previously described (Russmann, H., et al., *Science,* 281:565-8, 1998). In addition, we tested their delivery to class I and class II antigen presenting compartments by engineering surrogate "indicator epitopes" in the chimeric proteins. To monitor Class-I restricted immune responses we engineered the H-$2^b$ Class-I restricted epitope consisting of residues 366 through 374 from the influenza virus nucleoprotein ($IVNP_{366-374}$). To monitor Class-II restricted responses we utilized the I-$E^d$ epitope consisting of residues 85-104 of the vesicular stomatitis virus glycoprotein. Antigen delivery to antigen presenting cells was monitored using the T cell hybridomas 12.164 and 3DV315.14 (provided by Peter Docherty and Carol Reiss, respectively), which produce IL-2 upon presentation of the relevant peptides derived from the chimeric proteins expressed by *Salmonella*. These assays were carried out as previously described (Evans, D. T., et al., *J. Virol.,* 77:2400-2409, 2003; Russmann, H., et al., *Science,* 281:565-8, 1998). In addition, the constructs were tested for their ability to sensitize antigen-presenting cells for recognition by relevant T cells specific for the different tumor antigens.

Establishment of the Growth, Transportation and Storage Parameter that can Maintain the Immunogenicity of the Constructs in Preparation for Phase I Clinical Trials.

To comply with FDA regulations, growth of the different vaccine constructs is carried out in approved facilities. The different *Salmonella* vaccine constructs are grown at a remote site and subsequently transported to the location where the phase I clinical trials were conducted. The growth and transportation of the different vaccine strains has a very significant impact on their immunogenicity due to numerous environmental factors that influence the expression and function of the *Salmonella* type III secretion system that serves as the backbone for the antigen delivery system (Galán, J. E., et al., *Annu. Rev. Cell Dev. Biol.,* 17:53-86, 2001). Extensive studies are performed to identify growth and storage conditions that do not interfere with the immunogenicity of the different constructs. Bacterial strains grown under different conditions and stored following different protocols (e.g. freezing, lyophilization, etc.) are tested in the different in-vitro antigen-presenting assays to evaluate their antigen delivery potential.

Development of a *Salmonella*-Based System to Stimulate Innate Immunity Outputs and Localized Inflammation Within Tumors to Enhance the Antitumor Immune Response.

*Salmonella* spp. have the ability to stimulate potent inflammatory responses, which is the consequence of their ability to directly stimulate the innate immune system. It is this property that presumably makes *Salmonella* an effective antigen delivery system, given the demonstrated importance of the innate immune system in the generation of acquired immune responses. The benefits of the stimulation of innate immune and inflammatory responses within the tumor itself for the generation of specific immune responses to tumor antigens is well documented (Finn, O. J., et al., *Nat Rev Immunol.,* 3:630-41, 2003; Gilboa, E., *Nat Rev Cancer,* 4:401-411, 2004).

Therefore, a system to safely generate a localized and self-limiting inflammatory response within the tumor itself is developed. This system is based on the use of conditionally-lethal mutants of *S. typhimurium* that carry a deletion in the asd gene, which encodes for aspartate semialdehyde dehydrogenase (Galán, J. E., et al., *Gene,* 94:29-35, 1990). This gene is involved in the synthesis of diaminopimelic acid (DAP), an essential component of the peptidoglycan layer of the bacterial envelope. *S. typhimurium* Δasd can grow only if DAP is provided in the medium. Since mammals do not produce DAP, this strain cannot replicate within host tissues and therefore is completely avirulent. In the absence of DAP, *Salmonella* Δasd mutants can only replicate for a very limited number of generations until the pre-existing DAP within the bacteria is used up.

Whether the limited replication within the tumor is sufficient to induce a localized inflammatory response but not enough to generate side effects is tested. *S. typhimurium* strains carrying a deletion in the asd gene are constructed and tested using two well-characterized mouse models, one based on the human papilloma virus type 16 and the other the use of the methylcholanthrene induced sarcoma cms5. In the former, mice injected with cells expressing the E6 and E7 proteins of this virus develop tumors within three weeks of inoculation. Whether delivery of the E6 or E7 proteins by the *S. typhimurium* Δasd strain directly into the tumor increases the immune response to the tumor is investigated. In the latter, the tumor expresses a mutant form of ERK which is cloned into *S. typhimurium* Δasd and this construct tested with the view to evaluating a naturally occurring mouse antigen as a specific target. These experiments determine whether the stimulation of innate immunity and antigen presentation within the tumor increases the specific anti tumor immune response and results in its elimination. The number of generations that the *S. typhimurium* Δasd strain replicates is increased by administering DAP to the mice. We have previously used this strategy successfully to increase the replication of Δasd *S. typhimurium* mutants in a mouse model of infection.

REFERENCES

1. Scanlan, M. J., Simpson, A. J., and Old, L. J. 2004. The cancer/testis genes: review, standardization, and commentary. *Cancer Immun.* 4:1.
2. Van Der Bruggen, P., Zhang, Y., Chaux, P., Stroobant, V., Panichelli, C., Schultz, E. S., Chapiro, J., Van Den Eynde, B. J., Brasseur, F., and Boon, T. 2002. Tumor-specific shared antigenic peptides recognized by human T cells. *Immunol. Rev.* 188:51-64.
3. Wang, R. F., and Rosenberg, S. A. 1999. Human tumor antigens for cancer vaccine development. *Immunol. Rev.* 170:85-100.
4. Jager, E., Jager, D., and Knuth, A. 2003. Antigen-specific immunotherapy and cancer vaccines. *Int. J. Cancer.* 106: 817-820.
5. Belardelli, F., Ferrantini, M., Parmiani, G., Schlom, J., and Garaci, E. 2004. International meeting on cancer vaccines: how can we enhance efficacy of therapeutic vaccines? *Cancer Res.* 64:6827-6830.
6. Rosenberg, S. A., Yang, J. C., and Restifo, N. P. 2004. Cancer immunotherapy: moving beyond current vaccines. *Nat. Med.* 10:909-915.
7. Chen, Y. T., Scanlan, M. J., Sahin, U., Tureci, O., Gure, A. O., Tsang, S., Williamson, B., Stockert, E., Pfreundschuh, M., and Old, L. J. 1997. A testicular antigen aberrantly expressed in human cancers detected by autologous antibody screening. *Proc. Natl. Acad. Sci. U.S.A.* 94:1914-1918.
8. Sahin, U., Tureci, O., Schmitt, H., Cochlovius, B., Johannes, T., Schmits, R., Stemmer, F., Luo, G., Schobert, I., and Pfreundschuh, M. 1995. Human neoplasms elicit multiple specific immune responses in the autologous host. *Proc. Natl. Acad. Sci. U.S.A.* 92:11810-11813.
9. Jager, E., Chen, Y. T., Drijfhout, J. W., Karbach, J., Ringhoffer, M., Jager, D., Arand, M., Wada, H., Noguchi, Y., Stockert, E., et al. 1998. Simultaneous humoral and cellular immune response against cancer-testis antigen NY-ESO-1: definition of human histocompatibility leukocyte antigen (HLA)-A2-binding peptide epitopes. *J. Exp. Med.* 187:265-270.
10. Jungbluth, A. A., Chen, Y. T., Stockert, E., Busam, K. J., Kolb, D., Iversen, K., Coplan, K., Williamson, B., Altorki, N., and Old, L. J. 2001. Immunohistochemical analysis of NY-ESO-1 antigen expression in normal and malignant human tissues. *Int. J. Cancer* 92:856-860.
11. Pasare, C., and Medzhitov, R. 2003. Toll pathway-dependent blockade of CD4$^+$CD25$^+$ T cell-mediated suppression by dendritic cells. *Science* 299:1033-1036.
12. Pasare, C., and Medzhitov, R. 2004. Toll-dependent control mechanisms of CD4 T cell activation. *Immunity* 21:733-741.
13. Yang, Y., Huang, C. T., Huang, X., and Pardoll, D. M. 2004. Persistent Toll-like receptor signals are required for reversal of regulatory T cell-mediated CD8 tolerance. *Nat. Immunol.* 5:508-515.
14. Iwasaki, A., and Medzhitov, R. 2004. Toll-like receptor control of the adaptive immune responses. *Nat. Immunol.* 5:987-995.
15. Peng, G., Guo, Z., Kiniwa, Y., Voo, K. S., Peng, W., Fu, T., Wang, D. Y., Li, Y., Wang, H. Y., and Wang, R. F. 2005. Toll-like receptor 8-mediated reversal of CD4$^+$ regulatory T cell function. *Science* 309:1380-1384.
16. Kirby, A. C., Yrlid, U., and Wick, M. J. 2002. The innate immune response differs in primary and secondary *Salmonella* infection. *J. Immunol.* 169:4450-4459.
17. Wick, M. J. 2004. Living in the danger zone: innate immunity to *Salmonella*. *Curr. Opin. Microbiol.* 7:51-57.
18. Galán, J. E., Nakayama, K., and Curtiss, R., 3rd. 1990. Cloning and characterization of the asd gene of *Salmonella typhimurium*: use in stable maintenance of recombinant plasmids in *Salmonella* vaccine strains. *Gene* 94:29-35.
19. Russmann, H., Shams, H., Poblete, F., Fu, Y., Galán, J. E., and Donis, R. O. 1998. Delivery of epitopes by the *Salmonella* type III secretion system for vaccine development. *Science* 281:565-568.
20. Shams, H., Poblete, F., Russmann, H., Galán, J. E., and Donis, R. O. 2001. Induction of specific CD8$^+$ memory T cells and long lasting protection following immunization with *Salmonella typhimurium* expressing a lymphocytic choriomeningitis MHC class I-restricted epitope. *Vaccine* 20:577-585.
21. Evans, D. T., Chen, L. M., Gillis, J., Lin, K. C., Harty, B., Mazzara, G. P., Donis, R. O., Mansfield, K. G., Lifson, J. D., Desrosiers, R. C., et al. 2003. Mucosal priming of simian immunodeficiency virus-specific cytotoxic T-lymphocyte responses in rhesus macaques by the *Salmonella* type III secretion antigen delivery system. *J. Virol.* 77:2400-2409.
22. Kubori, T., and Galán, J. E. 2003. Temporal regulation of *salmonella* virulence effector function by proteasome-dependent protein degradation. *Cell* 115:333-342.
23. Lehmann, P. V., Forsthuber, T., Miller, A., and Sercarz, E. E. 1992. Spreading of T-cell autoimmunity to cryptic determinants of an autoantigen. *Nature* 358:155-157.
24. Vanderlugt, C. L., and Miller, S. D. 2002. Epitope spreading in immune-mediated diseases: implications for immunotherapy. *Nat. Rev. Immunol.* 2:85-95.
25. Lee, P. P., Yee, C., Savage, P. A., Fong, L., Brockstedt, D., Weber, J. S., Johnson, D., Swetter, S., Thompson, J., Greenberg, P. D., et al. 1999. Characterization of circulating T cells specific for tumor-associated antigens in melanoma patients. *Nat. Med.* 5:677-685.
26. van der Velden, A. W., Copass, M. K., and Stambach, M. N. 2005. *Salmonella* inhibit T cell proliferation by a direct, contact-dependent immunosuppressive effect. *Proc. Natl. Acad. Sci. USA* 102:17769-17774.

27. Galán, J. E., and Curtiss, R., 3rd. 1989. Virulence and vaccine potential of phoP mutants of *Salmonella typhimurium*. *Microb. Pathog.* 6:433-443.
28. Zhao, M., Yang, M., Li, X. M., Jiang, P., Baranov, E., Li, S., Xu, M., Penman, S., and Hoffman, R. M. 2005. Tumor-targeting bacterial therapy with amino acid auxotrophs of GFP-expressing *Salmonella typhimurium*. *Proc. Natl. Acad. Sci. U.S.A.* 102:755-760.
29. Avogadri, F., Martinoli, C., Petrovska, L., Chiodoni, C., Transidico, P., Bronte, V., Longhi, R., Colombo, M. P., Dougan, G., and Rescigno, M. 2005. Cancer immunotherapy based on killing of *Salmonella*-infected tumor cells. *Cancer Res.* 65:3920-3927.
30. Germeau, C., Ma, W., Schiavetti, F., Lurquin, C., Henry, E., Vigneron, N., Brasseur, F., Lethe, B., De Plaen, E., Velu, T., et al. 2005. High frequency of antitumor T cells in the blood of melanoma patients before and after vaccination with tumor antigens. *J. Exp. Med.* 201:241-248.
31. Lurquin, C., Lethe, B., De Plaen, E., Corbiere, V., Theate, I., van Baren, N., Coulie, P. G., and Boon, T. 2005. Contrasting frequencies of antitumor and anti-vaccine T cells in metastases of a melanoma patient vaccinated with a MAGE tumor antigen. *J. Exp. Med.* 201:249-257.
32. Galán, J. E. 2001. *Salmonella* interactions with host cells: type III secretion at work. *Annu. Rev. Cell. Dev. Biol.* 17:53-86.
33. Spiotto, M. T., Yu, P., Rowley, D. A., Nishimura, M. I., Meredith, S. C., Gajewski, T. F., Fu, Y. X., and Schreiber, H. 2002. Increasing tumor antigen expression overcomes "ignorance" to solid tumors via crosspresentation by bone marrow-derived stromal cells. *Immunity* 17:737-747.
34. Spiotto, M. T., Rowley, D. A., and Schreiber, H. 2004. Bystander elimination of antigen loss variants in established tumors. *Nat. Med.* 10:294-298.
35. Jager, E., Nagata, Y., Gnjatic, S., Wada, H., Stocked, E., Karbach, J., Dunbar, P. R., Lee, S. Y., Jungbluth, A., Jager, D., et al. 2000. Monitoring CD8 T cell responses to NY-ESO-1: correlation of humoral and cellular immune responses. *Proc. Natl. Acad. Sci. U.S.A.* 97:4760-4765.
36. Gnjatic, S., Nagata, Y., Jager, E., Stockert, E., Shankara, S., Roberts, B. L., Mazzara, G. P., Lee, S. Y., Dunbar, P. R., Dupont, B., et al. 2000. Strategy for monitoring T cell responses to NY-ESO-1 in patients with any HLA class I allele. *Proc. Natl. Acad. Sci. U.S.A.* 97:10917-10922.
37. Valmori, D., Dutoit, V., Lienard, D., Rimoldi, D., Pittet, M. J., Champagne, P., Ellefsen, K., Sahin, U., Speiser, D., Lejeune, F., et al. 2000. Naturally occurring human lymphocyte antigen-A2 restricted CD8+ T-cell response to the cancer testis antigen NY-ESO-1 in melanoma patients. *Cancer Res.* 60:4499-4506.
38. Lee, S. H., and Galán, J. E. 2004. *Salmonella* type III secretion-associated chaperones confer secretion-pathway specificity. *Mol. Microbiol.* 51:483-495.
39. Obert, S., O'Connor, R. J., Schmid, S., and Hearing, P. 1994. The adenovirus E4-6/7 protein transactivates the E2 promoter by inducing dimerization of a heteromeric E2F complex. *Mol. Cell. Biol.* 14:1333-1346.
40. Galán, J. E., Ginocchio, C., and Costeas, P. 1992. Molecular and functional characterization of the *Salmonella* invasion gene invA: homology of InvA to members of a new protein family. *J. Bacteriol.* 174:4338-4349.
41. Kaniga, K., Trollinger, D., and Galán, J. E. 1995. Identification of two targets of the type III protein secretion system encoded by the inv and spa loci of *Salmonella typhimurium* that have homology to the *Shigella* IpaD and IpaA proteins. *J. Bacteriol.* 177:7078-7085.
42. DeLeo, A. B., Shiku, H., Takahashi, T., John, M., and Old, L. J. 1977. Cell surface antigens of chemically induced sarcomas of the mouse. I. Murine leukemia virus-related antigens and alloantigens on cultured fibroblasts and sarcoma cells: description of a unique antigen on BALB/c Meth A sarcoma. *J. Exp. Med.* 146:720-734.
43. Ikeda, H., Ohta, N., Furukawa, K., Miyazaki, H., Wang, L., Kuribayashi, K., Old, L. J., and Shiku, H. 1997. Mutated mitogen-activated protein kinase: a tumor rejection antigen of mouse sarcoma. *Proc. Natl. Acad. Sci. U.S.A.* 94:6375-6379.
44. Mukai, K., Yasutomi, Y., Watanabe, M., Kenjo, A., Aota, T., Wang, L., Nishikawa, H., Ishihara, M., Fujita, T., Kuribayashi, K., et al. 2002. HER2 peptide-specific CD8+ T cells are proportionally detectable long after multiple DNA vaccinations. *Gene Ther.* 9:879-888.
45. Van Pel, A., De Plaen, E., and Boon, T. 1985. Selection of highly transfectable variant from mouse mastocytoma P815. *Somat. Cell. Mol. Genet.* 11:467-475.
46. Nishikawa, H., Tanida, K., Ikeda, H., Sakakura, M., Miyahara, Y., Aota, T., Mukai, K., Watanabe, M., Kuribayashi, K., Old, L. J., et al. 2001. Role of SEREX-defined immunogenic wild-type cellular molecules in the development of tumor-specific immunity. *Proc. Natl. Acad. Sci. U.S.A.* 98:14571-14576.
47. Nishikawa, H., Kato, T., Tanida, K., Hiasa, A., Tawara, I., Ikeda, H., Ikarashi, Y., Wakasugi, H., Kronenberg, M., Nakayama, T., et al. 2003. CD4+CD25+ T cells responding to serologically defined autoantigens suppress antitumor immune responses. *Proc. Natl. Acad. Sci. U.S.A.* 100:10902-10906.
48. Gnjatic, S., Atanackovic, D., Jager, E., Matsuo, M., Selvakumar, A., Altorki, N. K., Maki, R. G., Dupont, B., Ritter, G., Chen, Y. T., et al. 2003. Survey of naturally occurring CD4+ T cell responses against NY-ESO-1 in cancer patients: correlation with antibody responses. *Proc. Natl. Acad. Sci. U.S.A.* 100:8862-8867.
49. Niwa, H., Yamamura, K., and Miyazaki, J. 1991. Efficient selection for high-expression transfectants with a novel eukaryotic vector. *Gene* 108:193-199.
50. Miyahara, Y., Naota, H., Wang, L., Hiasa, A., Goto, M., Watanabe, M., Kitano, S., Okumura, S., Takemitsu, T., Yuta, A., et al. 2005. Determination of cellularly processed HLA-A2402-restricted novel CTL epitopes derived from two cancer germ line genes, MAGE-A4 and SAGE. *Clin. Cancer Res.* 11:5581-5589.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention. Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

We claim:

1. A method for stimulating an immune response against a first protein expressed by a tumor, comprising
administering to a subject in need of such treatment avirulent bacteria comprising a type III secretion system and a nucleic acid encoding a fusion protein that comprises an immunogenic second protein or an immunogenic fragment thereof fused to a polypeptide that is delivered by the type III secretion system of the avirulent bacteria, wherein the immunogenic second protein is an antigen against which the subject has preexisting CD8$^+$ T cells, wherein the fusion protein stimulates an immune response against the first protein and the immunogenic second protein.

2. A method for stimulating an immune response against a first protein expressed by a tumor, comprising
administering to a subject in need of such treatment an immunogenic second protein or an immunogenic fragment thereof to induce CD8$^+$ T cells against the immunogenic second protein, and
administering subsequently to the subject avirulent bacteria comprising a type III secretion system and a nucleic acid encoding a fusion protein that comprises the immunogenic second protein or immunogenic fragment thereof fused to a polypeptide that is delivered by the type III secretion system of the avirulent bacteria, wherein the fusion protein stimulates an immune response against the first protein and the immunogenic second protein.

3. The method of claim 1, wherein the immune response comprises a CD8$^+$ T cell response, a CD4$^+$ T cell response, or a CD8$^+$ T cell response and a CD4$^+$ T cell response.

4. The method of claim 1, wherein the immunogenic second protein or immunogenic fragment is a tumor antigen protein, a viral antigen protein, a microorganism antigen protein or an immunogenic fragment thereof.

5. The method of claim 1, wherein the avirulent bacteria are *Salmonella* spp., optionally *Salmonella enterica; Yersinia* spp.; *Bordetella* spp.; *Escherichia coli; Shigella* spp.; *Burkholderia mallei; Burkholderia pseudomallei*; or *Pseudomonas aeruginosa*.

6. The method of claim 5, wherein the avirulent *S. enterica* bacteria are *S. typhimurium*, optionally *S. typhimurium* ΔphoP phoQ ΔaroA Δasd.

7. The method of claim 1, wherein the stimulation of the immune response is an increased pre-existing immune response.

8. The method of claim 7, wherein the immune response comprises a CD8$^+$ T cell response, a CD4$^+$ T cell response, or a CD8$^+$ T cell response and a CD4$^+$ T cell response.

9. The method of claim 7, wherein the second immunogenic protein or immunogenic fragment is a tumor antigen protein, a viral antigen protein, a microorganism antigen protein or an immunogenic fragment thereof.

10. The method of claim 9, wherein more than one tumor antigen, viral antigen protein, microorganism antigen protein or immunogenic fragment thereof is encoded.

11. The method of claim 7, wherein the avirulent bacteria are *Salmonella* spp., optionally *Salmonella enterica; Yersinia* spp.; *Bordetella* spp.; *Escherichia coli; Shigella* spp.; *Burkholderia mallei; Burkholderia pseudomallei*; or *Pseudomonas aeruginosa*.

12. The method of claim 11, wherein the avirulent *S. enterica* bacteria are *S. typhimurium*, optionally *S. typhimurium* ΔphoP phoQ ΔaroA Δasd.

13. The method of claim 2, wherein the immune response is a CD4$^+$ T cell response, a CD8$^+$ T cell response, or both a CD4$^+$ T cell response and a CD8$^+$ T cell response.

14. The method of claim 2, wherein the second immunogenic protein or immunogenic fragment is a tumor antigen protein, viral antigen protein, microorganism antigen protein or an immunogenic fragment thereof.

15. The method of claim 14, wherein more than one tumor antigen protein, viral antigen protein, microorganism antigen protein or immunogenic fragment thereof is encoded.

16. The method of claim 2, wherein the avirulent bacteria are *Salmonella* spp., optionally *Salmonella enterica; Yersinia* spp.; *Bordetella* spp.; *Escherichia coli; Shigella* spp.; *Burkholderia mallei; Burkholderia pseudomallei*; or *Pseudomonas aeruginosa*.

17. The method of claim 16, wherein the avirulent *S. enterica* bacteria are *S. typhimurium*, optionally *S. typhimurium* ΔphoP phoQ ΔaroA Δasd.

18. The method of claim 2, wherein the avirulent bacteria are administered orally.

19. The method of claim 2, wherein the immunogenic second protein or an immunogenic fragment thereof is administered parenterally or orally.

20. The method of claim 2, wherein the stimulation of the immune response is an increased pre-existing immune response.

21. The method of claim 20, wherein the immune response comprises a $CD4^+$ T cell response, a $CD8^+$ T cell response, or a $CD4^+$ T cell response and a $CD8^+$ T cell response.

22. The method of claim 20, wherein the second immunogenic protein or immunogenic fragment is a second tumor antigen protein, a viral antigen protein, a microorganism antigen protein or an immunogenic fragment thereof.

23. The method of claim 22, wherein more than one tumor antigen protein, viral antigen protein, microorganism antigen protein or immunogenic fragment thereof is encoded.

24. The method of claim 20, wherein the avirulent bacteria are *Salmonella* spp., optionally *Salmonella enterica; Yersinia* spp.; *Bordetella* spp.; *Escherichia coli; Shigella* spp.; *Burkholderia mallei; Burkholderia pseudomallei*; or *Pseudomonas aeruginosa*.

25. The method of claim 24, wherein the avirulent *S. enterica* bacteria are *S. typhimurium*, optionally *S. typhimurium* ΔphoP phoQ ΔaroA Δasd.

26. The method of claim 20, wherein the avirulent bacteria are administered orally.

27. The method of claim 20, wherein the the second immunogenic protein or immunogenic fragment is administered parenterally or orally.

28. The method of claim 4, wherein more than one tumor antigen protein, viral antigen protein, microorganism antigen protein or immunogenic fragment thereof is encoded.

* * * * *